(12) United States Patent
Duggal et al.

(10) Patent No.: US 9,962,201 B2
(45) Date of Patent: May 8, 2018

(54) JOINT ARTHRODESIS AND ARTHROPLASTY

(71) Applicant: Musculoskeletal Innovations, LLC, Manlius, NY (US)

(72) Inventors: Neil Duggal, London (CA); Joshua Buttars, Chandler, AZ (US); Jeffery Arnett, Gilbert, AZ (US)

(73) Assignee: Musculoskeletal Innovations, LLC, Manlius, NY (US)

( * ) Notice: Subject to any disclaimer, the term of this patent is extended or adjusted under 35 U.S.C. 154(b) by 0 days. days.

(21) Appl. No.: 15/170,810

(22) Filed: Jun. 1, 2016

(65) Prior Publication Data

US 2016/0270829 A1 Sep. 22, 2016

Related U.S. Application Data

(63) Continuation of application No. 13/964,945, filed on Aug. 12, 2013, now Pat. No. 9,387,019, which is a
(Continued)

(51) Int. Cl.
*A61B 17/72* (2006.01)
*A61B 17/68* (2006.01)
(Continued)

(52) U.S. Cl.
CPC ...... *A61B 17/7266* (2013.01); *A61B 17/1775* (2016.11); *A61B 17/683* (2013.01);
(Continued)

(58) Field of Classification Search
CPC ............ A61B 17/1775; A61B 17/7258; A61B 17/844; A61B 17/7233; A61B 17/7291
See application file for complete search history.

(56) References Cited

U.S. PATENT DOCUMENTS 2,077,804 A * 4/1937 Morrison ............. A61B 17/742
411/340
2,489,870 A 11/1949 Dzus
(Continued)

FOREIGN PATENT DOCUMENTS

WO WO0130264 5/2001
WO WO0195818 12/2001
(Continued)

OTHER PUBLICATIONS

Thomas Martin Mueckley, M. D.; *Biomechanical Evaluation of Primary Stiffness of Tibiotalar Arthrodesis with an Intramedullary Compression Nail and Four Other Fixation Devices*, Foot & Ankle International vol. 27, No. 10/Oct. 2006 p. 814-820.
(Continued)

*Primary Examiner* — David Bates
(74) *Attorney, Agent, or Firm* — Maywood IP Law; Barbara Daniels; David Meibos

(57) ABSTRACT

An implantable fixation system for fusing a joint between a first bone and a second bone. The system may include an anchor, standoff, bolt, and cortical washer. The system may be implanted across the joint along a single trajectory, the length of the system adjustable to provide compressive force between the anchor and the cortical washer. The system may be implanted across a tibiotalar joint with the anchor positioned in the sinus tarsi. A spacing member may be inserted between the two bones and the fixation system implanted to extend through an opening in the spacing member. The spacing member may be anatomically shaped and/or provide deformity correction. An ankle arthroplasty system may include a tibial plate, a talar plate, and a bearing insert. The plates may be anchored to the tibia and talus along a single trajectory. The ankle arthroplasty system may be revisable to a fusion system.

12 Claims, 35 Drawing Sheets

Related U.S. Application Data continuation of application No. 12/835,032, filed on Jul. 13, 2010, now Pat. No. 8,585,744.

(60) Provisional application No. 61/225,398, filed on Jul. 14, 2009, provisional application No. 61/254,500, filed on Oct. 23, 2009, provisional application No. 61/254,512, filed on Oct. 23, 2009, provisional application No. 61/323,156, filed on Apr. 12, 2010, provisional application No. 61/323,170, filed on Apr. 12, 2010, provisional application No. 61/356,948, filed on Jun. 21, 2010.

(51) Int. Cl.
*A61F 2/42* (2006.01)
*A61B 17/17* (2006.01)

(52) U.S. Cl.
CPC ...... *A61B 17/7225* (2013.01); *A61B 17/7233* (2013.01); *A61B 17/7291* (2013.01); *A61F 2/4202* (2013.01); *A61B 17/1725* (2013.01); *A61F 2002/4205* (2013.01); *A61F 2002/4207* (2013.01)

(56) References Cited

U.S. PATENT DOCUMENTS

| | | | |
|---|---|---|---|
| 2,511,051 A | 6/1950 | Dzus | |
| 3,763,855 A | 10/1973 | McAtee | |
| 5,098,433 A * | 3/1992 | Freedland | A61B 17/68 606/60 |
| 5,769,852 A | 6/1998 | Brånemark | |
| 5,855,579 A | 1/1999 | Russell | |
| 5,964,768 A | 10/1999 | Huebner | |
| 6,027,504 A | 2/2000 | McGuire | |
| 6,197,029 B1 * | 3/2001 | Fujimori | A61B 17/68 606/62 |
| 6,210,414 B1 | 4/2001 | Lin | |
| 6,302,887 B1 | 10/2001 | Spranza | |
| 6,547,791 B1 | 4/2003 | Hofmann | |
| 6,579,293 B1 * | 6/2003 | Chandran | A61B 17/1725 606/62 |
| 6,663,669 B1 | 12/2003 | Reiley | |
| 6,673,116 B2 | 1/2004 | Reiley | |
| 6,860,885 B2 | 3/2005 | Bonutti | |
| 6,860,902 B2 | 3/2005 | Reiley | |
| 6,875,236 B2 | 4/2005 | Reiley | |
| 6,926,739 B1 | 8/2005 | Giannini | |
| 7,314,488 B2 | 1/2008 | Reiley | |
| 7,410,488 B2 * | 8/2008 | Janna | A61B 17/72 606/62 |
| 7,534,246 B2 | 5/2009 | Mauldin | |
| 7,641,697 B2 | 1/2010 | Reiley | |
| 7,985,255 B2 | 7/2011 | Bray | |
| 2002/0055744 A1 * | 5/2002 | Reiley | A61B 17/15 606/79 |
| 2003/0097131 A1 * | 5/2003 | Schon | A61B 17/72 606/62 |
| 2004/0039394 A1 | 2/2004 | Conti | |
| 2004/0153153 A1 | 8/2004 | Elson | |
| 2005/0107791 A1 * | 5/2005 | Manderson | A61B 17/68 606/62 |
| 2005/0125070 A1 | 6/2005 | Reiley | |
| 2005/0240189 A1 | 10/2005 | Rousseau | |
| 2005/0288792 A1 | 12/2005 | Landes | |
| 2006/0235394 A1 | 10/2006 | Martin | |
| 2006/0264944 A1 | 11/2006 | Cole | |
| 2006/0264950 A1 | 11/2006 | Mazur | |
| 2007/0112432 A1 | 5/2007 | Reiley | |
| 2007/0179621 A1 | 8/2007 | McClellan | |
| 2007/0233100 A1 | 10/2007 | Metzinger | |
| 2007/0233101 A1 | 10/2007 | Metzinger | |
| 2007/0233102 A1 | 10/2007 | Metzinger | |
| 2007/0233103 A1 | 10/2007 | Metzinger | |
| 2007/0233104 A1 | 10/2007 | Metzinger | |
| 2007/0270846 A1 | 11/2007 | Metzinger | |
| 2007/0288097 A1 | 12/2007 | Hurowitz | |
| 2008/0065227 A1 | 3/2008 | Reiley | |
| 2008/0147190 A1 | 6/2008 | Dewey | |
| 2008/0221577 A1 * | 9/2008 | Elghazaly | A61B 17/7241 606/64 |
| 2009/0018660 A1 | 1/2009 | Roush | |
| 2009/0082875 A1 | 3/2009 | Long | |
| 2009/0138096 A1 | 5/2009 | Myerson | |
| 2009/0149861 A1 * | 6/2009 | Brodsky | A61B 17/1725 606/96 |
| 2009/0182433 A1 | 7/2009 | Reiley | |
| 2009/0240338 A1 | 9/2009 | Reiley | |
| 2009/0326533 A1 | 12/2009 | Dell Oca | |
| 2010/0010490 A1 | 1/2010 | Brigido | |
| 2011/0282346 A1 * | 11/2011 | Pham | A61B 17/7208 606/62 |
| 2013/0325006 A1 * | 12/2013 | Michelinie | A61B 17/7291 606/62 |

FOREIGN PATENT DOCUMENTS

| | | |
|---|---|---|
| WO | WO03017822 | 3/2003 |
| WO | WO2004028383 | 4/2004 |
| WO | WO2006091460 | 8/2006 |
| WO | WO2007120539 | 10/2007 |
| WO | WO2009108194 | 9/2009 |

OTHER PUBLICATIONS

Takahiro Niikura, M.D. *Ankle Arthrodesis Using Antegrade Intramedullary Nail for Salvage o Nonreconstructable Tibial Pilon Fractures*, http://www.orthosupersite.com/print.asp?rID=41937, Oct. 6, 2009.

Edward S. Holt, M.D., *Ankle Arthrodesis Using Internal Screw Fixation*, Clinical Orthopaedics and Related Research; No. 268 Jul. 1991 p. 21-28.

John M. Schuberth, The *Tripod Fixation Technique for Ankle Arthrodesis*, The Journal of Foot & Ankle Surgery; vol. 48, No. 1, Jan./Feb. 2009 p. 93-96.

Thit Lwin, MBBS, *Tibio-Talo-CAlcaneal Fusion Using SIGN IM Nail*, Techniques in Orthopaedics; vol. 24, No. 4, 2009 p. 277-278.

Robert L. Friedman M.D., *A Biomechanical Comparative Analysis of Two Techniques for Tibiotalar Arthrodesis*, Foot & Ankle International; vol. 15, No. 6/Jun. 1994 p. 301-305.

Scott Nasson, M.D, *Biomechanical Comparison of Ankle Arthrodesis Techniques: Crossed Screws vs. Blade Plate*, Foot & Ankle International; vol. 22, No. 7/Jul. 2001 p. 575-580.

Lowell H. Gill, M.D., *Challenges in Total Ankle Arthroplasty*, Foot & Ankle International vol. 25, No. 4/Apr. 2004, p. 195-207.

Ivan S. Tarkin, M.D., *Anterior Plate Supplementation Increases Ankle Arthrodesis Construct Rigidity*, Foot & Ankle International Vo. 28, No. 2/Feb. 2007, p. 219-223.

Tara Parker-Pope, *Ankles Gain as Candidates for Joint Replacement*, The New York Times; Well Blog—NYTimes.comhttp://well.blogs.nytimes.com/2010/01/18/ankles-gain-as-candidates-for-joint-replacement; Jan. 18, 2010 4:09 PM, p. 1-3.

Prof. Dr. Beat Hintermann, *Anatomic and Biomechanical Characteristics of the Ankle Joint and Total Ankle Arthroplasty*, Total Ankle Arthroplasty, Oct. 2004; Chpt. 4, p. 25-42.

Prof. Dr. Beat Hintermann, *History of Total Ankle Arthroplasty*, Total Ankle Arthroplasty, Oct. 2004; Chpt. 5, p. 43-57.

Prof. Dr. Beat Hintermann, *Current Designs of Total Ankle Prostheses*, Total Ankle Arthroplasty, Oct. 2004; Chpt. 6. p. 59-89.

Prof. Dr. Beat Hintermann, *Surgical Techniques*, Total Ankle Arthroplasty, Oct. 2004; Chpt. 8, p. 105-125.

Prof. Dr. Beat Hintermann, *Postoperative Care and Follow-Up*, Total Ankle Arthroplasty, Oct. 2004; Chpt. 9, p. 127-133.

Prof. Dr. Beat Hintermann, *What is Feasible in Total Ankle Arthroplasty*, Total Ankle Arthroplasty, Oct. 2004; Chpt. 10, p. 135-162.

(56) References Cited

OTHER PUBLICATIONS

Prof. Dr. Beat Hintermann, *Complications of Total Ankle Arthroplasty*, Total Ankle Arthroplasty, Oct. 2004; Chpt. 11, p. 163-184.

* cited by examiner

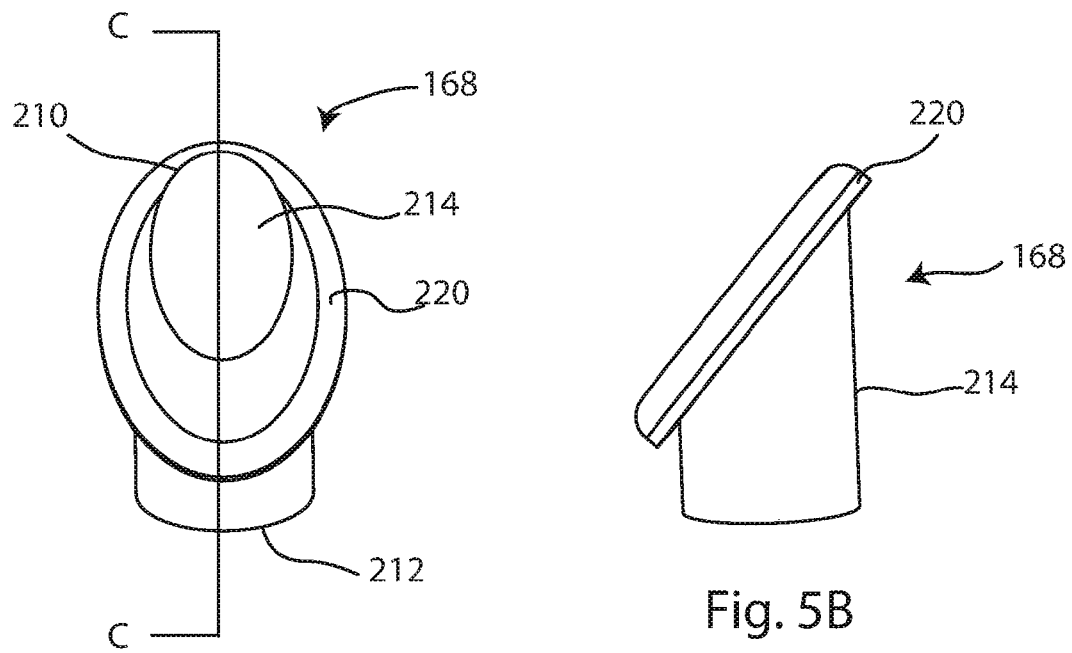
Fig. 5A
Fig. 5B
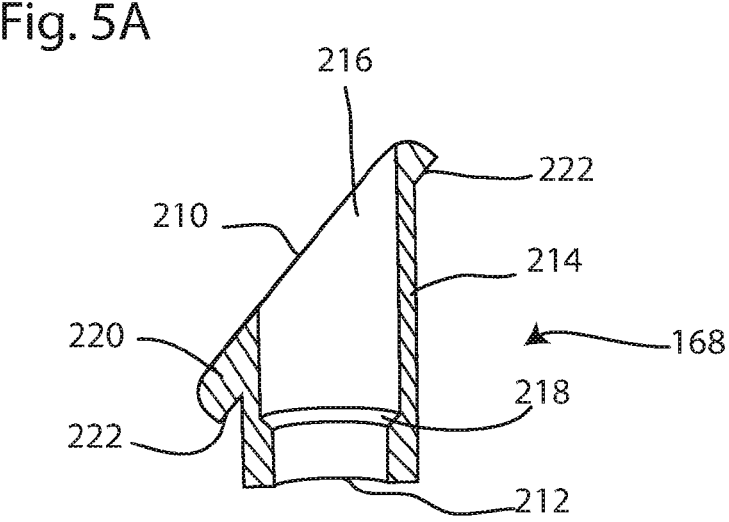
Fig. 5C

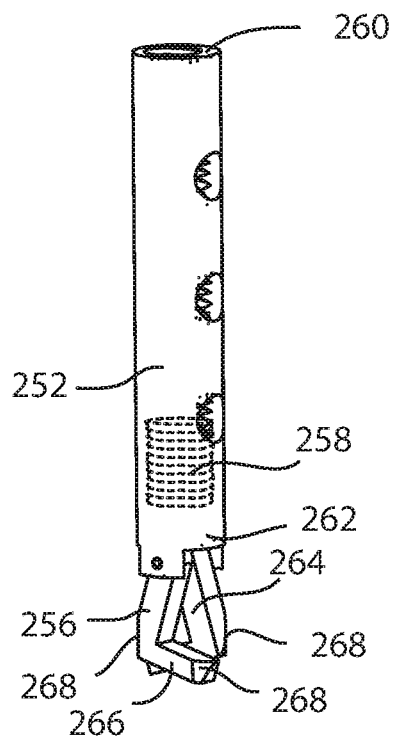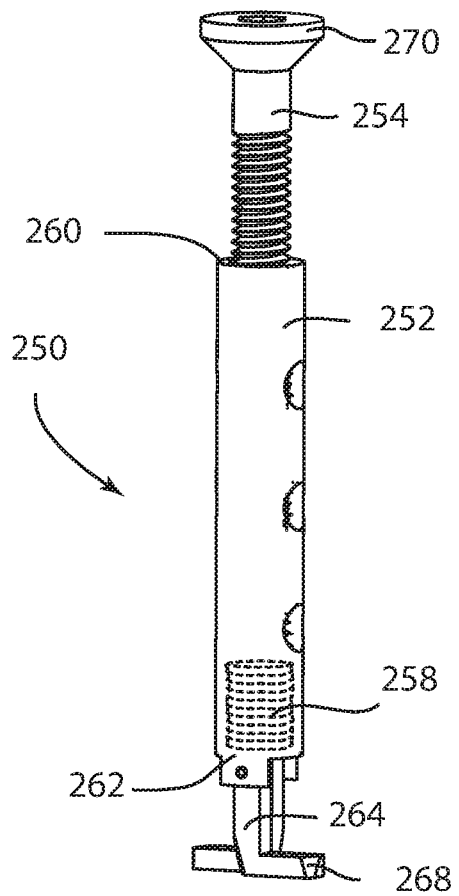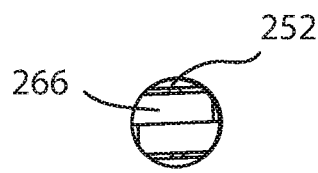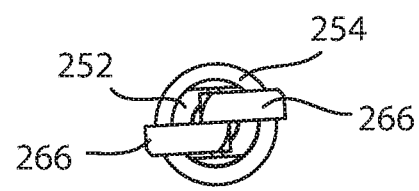
Fig. 11A
Fig. 11C
Fig 11B
Fig. 11D

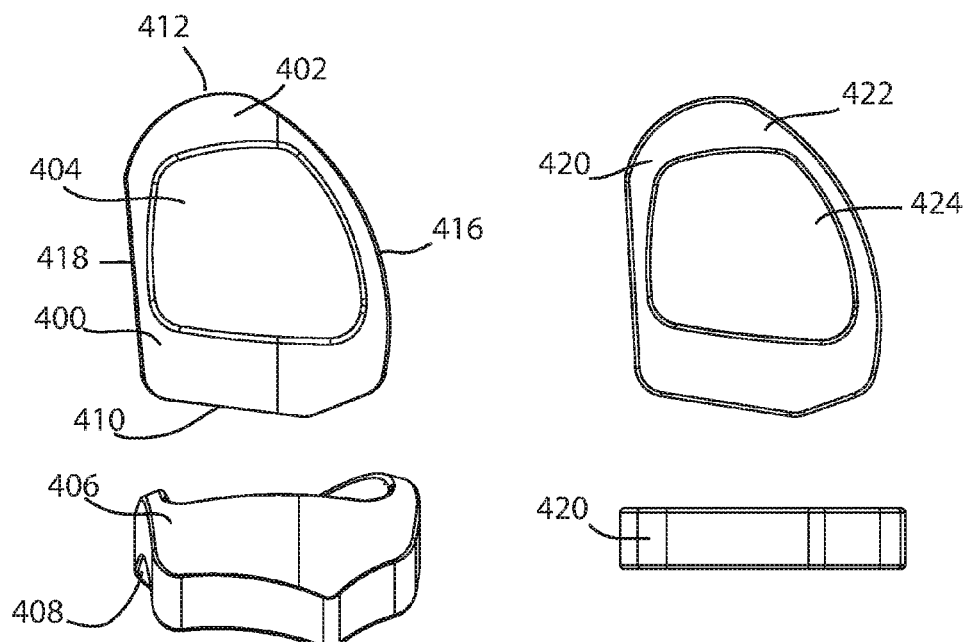
Fig. 18A
Fig. 18B
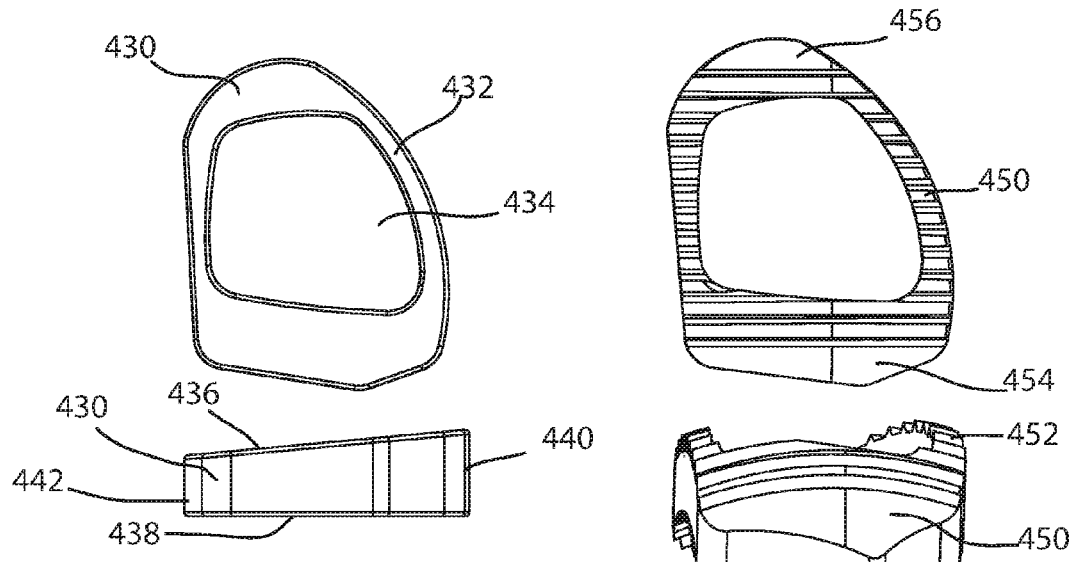
Fig. 18C
Fig. 18D

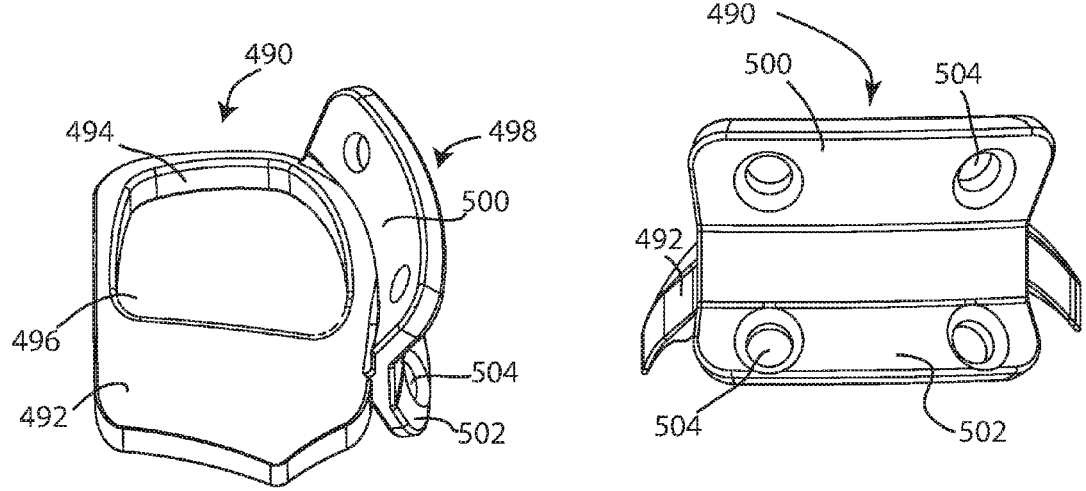
Fig. 21A
Fig. 21B
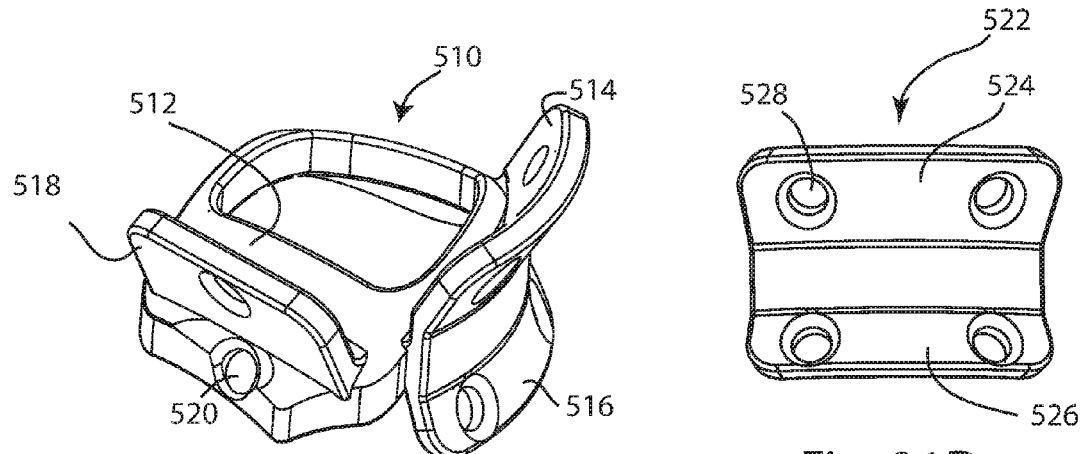
Fig. 21C
Fig. 21D

JOINT ARTHRODESIS AND ARTHROPLASTY

CROSS-REFERENCE TO RELATED APPLICATIONS

This application is a continuation of pending U.S. patent application Ser. No. 13/964,945, filed Aug. 12, 2013, and is entitled JOINT ARTHRODESIS AND ARTHROPLASTY, which is a continuation of:

U.S. patent application Ser. No. 12/835,032, filed Jul. 13, 2010, now patented as U.S. Pat. No. 8,585,744, and is entitled JOINT ARTHRODESIS AND ARTHROPLASTY.

U.S. patent application Ser. No. 12/835,032 claims the benefit of the following:

U.S. Provisional Patent Application No. 61/225,398, filed Jul. 14, 2009, and is entitled MODULAR ANKLE HEMI-ARTHROPLASTY;

U.S. Provisional Patent Application No. 61/254,500, filed Oct. 23, 2009, and is entitled SYSTEMS AND METHODS FOR ANKLE REPLACEMENT, ANKLE FUSION AND HINDFOOT FUSION;

U.S. Provisional Patent Application No. 61/254,512, filed Oct. 23, 2009, and is entitled SYSTEMS AND METHODS FOR WRIST ARTHROPLASTY AND WRIST FUSION;

U.S. Provisional Patent Application No. 61/323,156, filed Apr. 12, 2010, and is entitled ANKLE INTRAMEDULLARY ARTHRODESIS AND ARTHOPLASTY SYSTEM;

U.S. Provisional Patent Application No. 61/323,170, filed Apr. 12, 2010, and is entitled FUSION METHODS AND DEFORMITY CORRECTION SYSTEM; and U.S. Provisional Patent Application No. 61/356,948, filed Jun. 21, 2010, and is entitled ANKLE SPACER AND FIXATION.

The above-identified documents are incorporated herein by reference.

FIELD OF THE INVENTION

This invention relates to surgical implants which provide joint arthrodesis or arthroplasty. Specifically, this invention relates to implants for ankle arthrodesis or arthroplasty.

BACKGROUND OF THE INVENTION

Ankle arthritis is common following a traumatic injury such as an ankle fracture, ligament injury or failed open reduction internal fixation. Arthritis is also seen in patients with rheumatoid arthritis and in diabetic patients with charcot arthropathy. In comparison to most patients affected by hip and knee arthritis, ankle arthritis patients are usually younger and have often had prior ankle surgery. The treatment goal is to provide pain relief. Currently, patients with ankle arthritis are presented with either fusion or arthroplasty as surgical options.

A fusion, or arthrodesis, is an effective solution for pain resulting from ankle arthritis and has been the historical gold standard for treatment. An arthrodesis is currently the recommended option for patients with diabetic charcot arthropathy, post traumatic patients with poor bone stock, and in the young active patient with arthritis. Arthrodesis is also a surgical option following failed ankle arthroplasty. An ankle arthroplasty is another possible solution for ankle arthritis, and often involves a replacement of the distal tibia and/or a portion of the talus. However, problems exist with some of the current systems for ankle arthrodesis and arthroplasty.

Current systems that perform ankle fusion fixation have certain disadvantages. First, some cannulated screws have been complicated by hardware failure prior to complete fusion, as well as lack of adequate compression across the fusion site. Depending on the orientation of screw insertion, the screws may not restrict motion in the plane of motion of the joint and therefore increase the likelihood of development of nonunion. Second, some plate systems are often able to accommodate deformity in only one plane, and also can cause prominence that leads to postoperative skin irritation. Third, some hindfoot fusion nails have been inserted retrograde to treat ankle arthritis. Insertion of the retrograde nail will sacrifice the subtalar joint even though the joint may not be affected by arthritis. Current retrograde fusion nails are not designed to specifically fuse the posterior facet of the subtalar joint. A common complication of current retrograde systems involves a nonunion of the posterior facet joint because they do not specifically fuse this area with the fusion nail. The plantar skin incision that is required for the retrograde nail has been associated with wound complications and injury to the plantar branch of the tibial nerve. Many of these forms of ankle arthrodesis require an 8 to 12 week period of strict non weight bearing to ensure fusion, and patient compliance with non weight bearing is often difficult to achieve.

The current generation of ankle arthroplasty systems presents disadvantages resulting in poor patient outcomes. Current ankle arthroplasty may not be a viable option for patients who have poor bone stock. These patients include those who have undergone past operative procedures for fractures and diabetic patients with charcot arthropathy. Poor bone stock in the distal tibia and talus can result in implant malposition and failure. Second, traditional ankle arthroplasty may not be an ideal option for the young and active patient because of the risk of increased wear and early implant failure. Third, many current total ankle arthroplasty systems require resection of a significant amount of bone from both the tibia and talus in order to create a space for insertion of the implants. These large bone cuts can create a large void to fill if the ankle replacement fails. A fusion following an arthroplasty with large bone cuts is often complicated by an increased rate of nonunion.

Therefore, the need exists for improved ankle arthrodesis and arthroplasty systems. An arthrodesis system which provides improved compression across the fusion site and/or structural bone support may result in improved long-term fusion and pain relief. An arthrodesis or arthroplasty system which relies on anchoring or fixation on strong outer cortical bone instead of compromised bone stock may provide an increased rate of union, or longer lasting wear, respectively. An arthroplasty system which requires minimal resection may result in enhanced comfort and mobility. An arthroplasty convertible to a fusion system with minimal disturbance of surrounding tissues may result in better union following the fusion.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 2 is an antero-lateral view of a partial foot, ankle and lower leg with two compression bolt systems implanted across the tibiotalar joint;

FIG. 5A is a front view of the cortical washer of FIG. 4B; FIG. 5B is a side view of the cortical washer of FIG. 4B; and FIG. 5C is a cross-sectional view of the cortical washer of FIG. 4B, taken along line C-C in FIG. 5A;

FIG. 9 illustrates the compression bolt system of FIG. 6 implanted across a tibiotalar joint in a bone bore extending obliquely through a distal tibia and talus, the anchor disposed in the sinus tarsi inferior to the talus;

FIG. 11A is an isometric view of a standoff, set screw and paired L-shaped tabs of a compression bolt system, with the paired tabs in an insertion configuration; FIG. 11B is a bottom view of the paired tabs and standoff of FIG. 11A in the insertion configuration, and a compression bolt; FIG. 11C is an isometric view of the system of FIG. 11A with the set screw and paired tabs in a deployed configuration; FIG. 11D is a bottom view of the compression bolt, paired tabs and standoff of FIG. 11C in the deployed configuration;

FIG. 14 illustrates the targeting guide system of FIG. 12 guiding a guide wire along a first trajectory through a tibia and a talus;

FIG. 15 illustrates the targeting guide system of FIG. 12 with the driver of FIG. 13C driving a standoff of a first compression bolt system into engagement with a nut held on the anchor positioning arm of the guide system, along the preferred trajectory of FIG. 14;

FIG. 16 illustrates the fully implanted first compression bolt system implanted along the first trajectory of FIG. 14, and the targeting system of FIG. 12 repositioned along a second trajectory through the tibia and talus, with the driver driving a standoff of a second compression bolt system into engagement with a nut held on the anchor positioning arm of the guide system;

FIG. 17 is a medial view of a tibia, talus and calcaneus illustrating a compression bolt system implanted across the tibiotalar joint and anchored in the sinus tarsi, with a supplementary stabilizing screw implanted across the joint;

FIG. 18A is a superior and a front view of an anatomic spacing member shaped to fit on the superior side of a talus; FIG. 18B is a superior and a front view of a flat spacing member; FIG. 18C is a superior and a front view of a wedge-shaped spacing member; and FIG. 18D is a superior and a front view of an toothed spacing member having bone-engaging ridges;

FIG. 19 is a medial view of a tibia, talus and calcaneus with an implanted bone support implant system, the system including the toothed spacing member of FIG. 18D implanted between the talus and the tibia, and a compression bolt system implanted across the tibiotalar joint and anchored in the sinus tarsi;

FIG. 21A is an isometric view of a spacing member including lateral fixation flanges; FIG. 21B is a lateral view of the spacing member of FIG. 21A; FIG. 21C is an isometric view of a spacing member including lateral fixation flanges and an anterior fixation flange; FIG. 21D is an isometric view of a plate member;

FIG. 23 is an anterior view of the spacing member of FIG. 20A implanted between a talus and a tibia, with a compression bolt system implanted to extend from an exterior surface of the tibia, through a fixation aperture in the spacing member, to the exterior surface of the talus in the sinus tarsi;

FIG. 24 is a lateral view of a the spacing member of FIG. 22A implanted between a talus and a tibia, the fibula not shown for clarity, with a compression bolt system implanted across the tibiotalar joint and through a window of the spacing member, and a supplementary stabilization screw implanted along a different trajectory than the compression bolt system;

FIG. 30 is an anterior view of the targeting guide system of FIG. 29A positioned to guide a guidewire through a tibia and talus along a selected trajectory to a guide arm disposed in the sinus tarsi;

FIG. 31 is an antero-lateral view of a tibia, talus, and calcaneus, illustrating a resected tibial space and a prepared bone bore extending through the tibia and the talus;

FIG. 33 is an antero-lateral view of a tibia, talus, and calcaneus with the ankle arthroplasty system of FIG. 25 implanted in the resected tibial space and prepared bone bore;

FIG. 35 is an antero-lateral view of a tibia, talus, and calcaneus, with an anchor implanted in the talus, showing a method for implantation of the spacing member of FIG. 34A and implantation of a compression bolt system across the tibiotalar joint;

FIG. 36 is an anterior view of the tibia and talus of FIG. 35 with the implanted spacing member and compression bolt system, and a plurality of supplementary fasteners implanted to provide additional cross-fixation of the system in the tibia and the talus; and FIG. 37 is a posterior view of a tibia, talus, and calcaneus with a bone fixation system comprising an intramedullary nail and an anchor implanted across the tibiotalar joint.

DETAILED DESCRIPTION OF THE PREFERRED EMBODIMENTS

Figure 1:
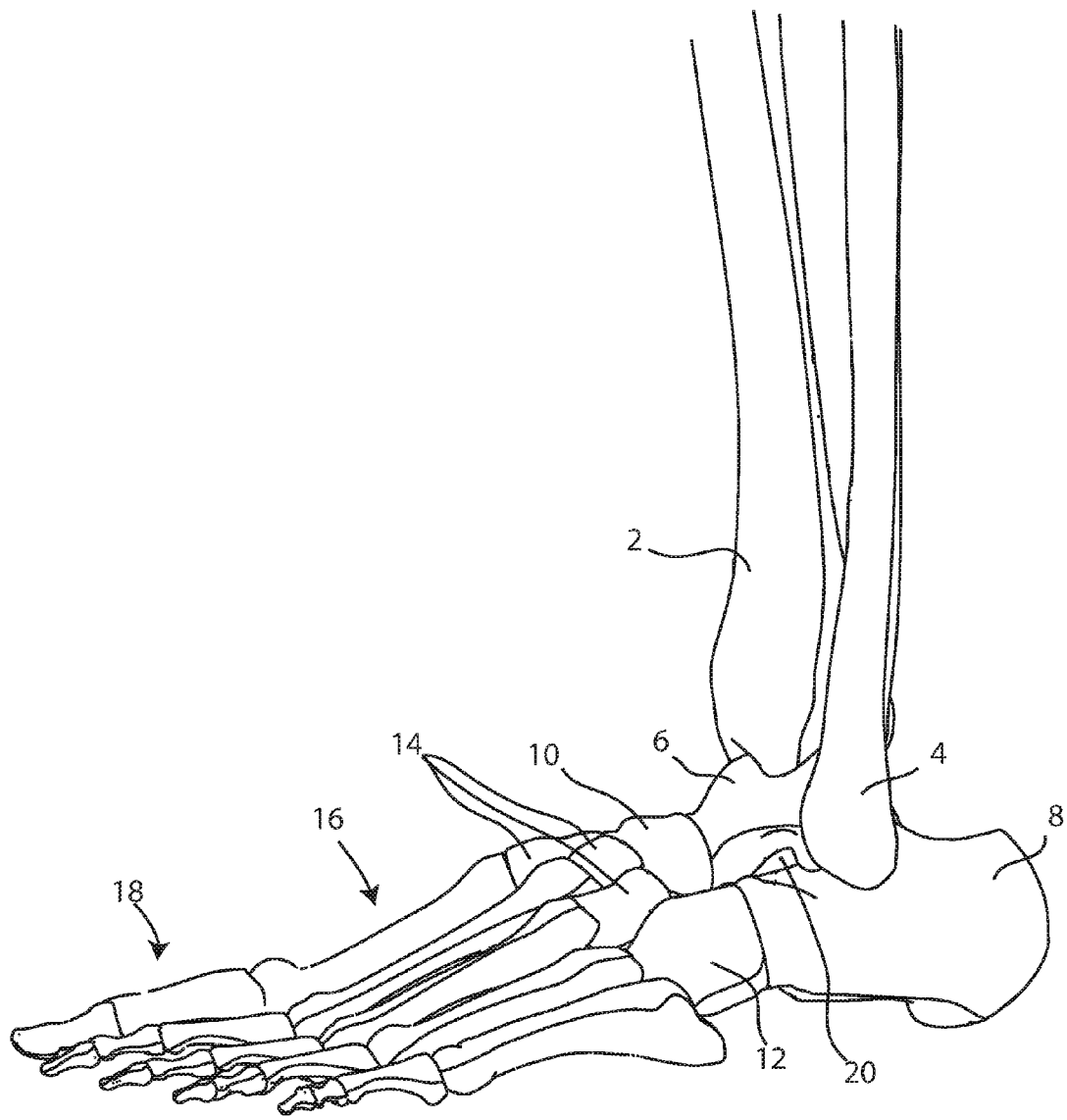
FIG. 1 is an antero-lateral view of a left foot, ankle and lower leg skeleton.

The present invention relates to implants for ankle arthrodesis and/or arthroplasty. Those of skill in the art will recognize that the following description is merely illustrative of the principles of the invention, which may be applied in various ways to provide many different alternative embodiments. This description is made for the purpose of illustrating the general principles of this invention and is not meant to limit the inventive concepts in the appended claims.

One embodiment of the invention may be an implantable bone fixation system for providing compression between a first exterior bone surface and a second exterior bone surface. The bone fixation system may include a first elongated structure, a second elongated structure, and an anchor. The first elongated structure may have a head and a shaft, the head shaped to bear against the first exterior bone surface. The second elongated structure may have a proximal end, a distal end, a longitudinal axis extending between the proximal end and the distal end, and an external diameter perpendicular to the longitudinal axis. The anchor may be disposed at the distal end of the second elongated structure, and have a deployed configuration in which a portion of the anchor protrudes beyond the external diameter of the second elongated structure. The anchor may be shaped to bear against the second exterior bone surface. The shaft of the first elongated structure may be coaxially received by the proximal end of the second elongated structure and may be selectively adjustable relative to the second elongated structure to increase or decrease a distance between the head and the anchor to provide a selected level of compression between the first exterior bone surface and the second exterior bone surface. The bone fixation system may further have an insertion configuration, the anchor selectively movable relative to the second elongated structure between the insertion configuration and the deployed configuration.

The anchor may include a toggle attached to the distal end of the second elongated structure, the toggle selectively deployable between an insertion configuration and the deployed configuration. In the deployed configuration the toggle is freely pivotable relative to distal end of the second elongated structure.

The anchor may include a plurality of tabs attached to the distal end of the second elongated structure, the tabs selectively deployable between an insertion configuration and the deployed configuration. In the deployed configuration a portion of each tab protrudes beyond the external diameter of the second elongated structure.

The anchor may have a vertical axis and a transverse axis perpendicular to the vertical axis. The anchor may further include a convex bearing surface shaped to bear congruently against the second exterior bone surface; and a connection feature shaped to receive a portion of the second elongated structure to attach the anchor to the second elongated structure, the connection feature obliquely oriented relative to at least one of the vertical axis and the transverse axis.

The first elongated structure may include an externally threaded bolt and the second elongated structure may include a standoff having a threaded bore. The bolt is receivable in the standoff bore and is threadably adjustable relative to the standoff bore to provide the selected level of compression between the first exterior bone surface and the second exterior bone surface.

The head of the first elongated member may include a cortical washer, the cortical washer having a rim shaped to bear congruently against the first exterior bone surface and a bore shaped to retain the shaft of the first elongated member.

The system may further include a spacing member having a peripheral body wall and a bore extending therethrough, the spacing member shaped to be inserted between a first bone and a second bone to provide load-bearing support between the first bone and the second bone.

A method of implanting a bone fixation system may include inserting a first elongated structure into an opening in a first exterior bone surface on a first bone, the first elongated structure comprising a head and a shaft; inserting a second elongated structure into the opening, the second elongated structure having a proximal end, and a distal end, and having a longitudinal axis extending between the proximal end and the distal end, and an external diameter perpendicular to the longitudinal axis. The method may include coaxially receiving the first elongated structure with the second elongated structure, moving an anchor positioned at the distal end of the second elongated structure into a deployed configuration in which a portion of the anchor protrudes beyond the external diameter of the second elongated structure, and adjusting the first elongated structure relative to the second elongated structure to change a distance between the head and the anchor to provide a selected level of compression between the first exterior bone surface and the second exterior bone surface.

The method may include moving the first elongated structure along the longitudinal axis to adjust the first elongated structure relative to the second elongated structure. The first elongated structure may include an externally threaded bolt and the second elongated structure may include an internally threaded standoff. The method may further include rotating the bolt within the standoff to adjust the first elongated structure relative to the second elongated structure. The method may further include engaging a set screw with the second elongated structure to urge the anchor into the deployed configuration. The anchor may have a vertical axis and a transverse axis perpendicular to the vertical axis, so that moving the anchor into the deployed configuration includes moving the anchor into an orientation in which the transverse axis of the anchor is at an oblique angle relative to the longitudinal axis of the second elongated structure.

The method may include inserting a cortical washer into the opening in the first exterior bone surface such that a rim of the cortical washer bears congruently against the first exterior bone surface, inserting the first elongated structure into the bore of the cortical washer; and retaining the head of the first elongated structure with the bore of the cortical washer.

The method may include inserting a spacing member having a peripheral body wall and a bore extending therethrough into a space between the first bone and the second bone to provide load-bearing support between the first bone and the second bone.

The method may include positioning a mobility structure between the first elongated structure and the anchor to allow relative motion between the first bone and the second bone.

The method may include creating a straight elongated bore extending from the opening in the first exterior bone surface to the second exterior bone surface along a trajectory oblique to the intramedullary canal of the first bone, inserting the first elongated structure along the trajectory, and inserting the second elongated structure along the trajectory.

Another embodiment of the invention may be a bone anchor system implantable to extend between a first exterior bone surface and a second exterior bone surface, the bone anchor system including an elongated structure having a first end and a second end, the elongated structure insertable through bone such that the first end is disposed at the first exterior bone surface and the second end is disposed at the second exterior bone surface, and an anchor member removably attachable to the second end of the elongated structure, the anchor having a vertical axis and a transverse axis perpendicular to the vertical axis. The anchor member may include a curved bearing surface shaped to bear congruently against the second exterior bone surface, a connection feature obliquely oriented relative to at least one of the vertical axis and the transverse axis, and a base surface disposed opposite the convex bearing surface, the base surface shaped to avoid destructive contact with neighboring bone structures when the anchor member is attached to the elongated structure and the convex bearing surface bears against the second exterior bone surface.

The elongated structure second end may include an externally threaded hub and the connection feature may include a threaded bore, the threaded hub is engageable in the threaded bore to attach the anchor member to the elongated structure.

The elongated structure may have a longitudinal axis extending from the first end to the second end, and an external diameter perpendicular to the longitudinal axis, so that when the anchor member is attached to the second end of the elongated structure the transverse axis of the anchor member is at an oblique angle relative to the longitudinal axis of the elongated structure. The curved bearing surface may extend radially beyond the external diameter of the elongated structure when the anchor member is attached to the second end of the elongated structure. The curved bearing surface may be convex, and the curved bearing surface may be convexly curved about the transverse axis of the anchor member, the convex curve having a constant radius along the length of the transverse axis.

The elongated structure may include a bolt and a standoff, the bolt coaxially received by the standoff and selectively adjustable relative to standoff to increase or decrease a distance between the first end of the elongated structure and the anchor to provide a selected level of compression between the first exterior bone surface and the second exterior bone surface.

The bone anchor system may further include a cortical washer having a rim shaped to bear congruently against the first exterior bone surface, and a bore configured to retain the first end of the elongated structure.

The anchor member may be sized and shaped to be inserted into a sinus tarsi between a talus and a calcaneus, the curved bearing surface shaped to bear congruently against the inferior surface of the talus within the sinus tarsi.

Another embodiment of the invention may be a bone support implant system including a first bone anchoring device and a spacing member. The first bone anchoring device may have a first end attachable to a first exterior bone surface on the first bone and a second end attachable to a second exterior bone surface on the second bone. The spacing member may have a peripheral body wall and a bore extending therethrough and be shaped to be inserted between the first bone and the second bone to provide load-bearing support between the first bone and the second bone. The first bone anchoring device may be configured to extend through the first bone, through the spacing member bore, and through the second bone to provide compression between the first exterior bone surface and the second exterior bone surface.

The bone support implant system may further include a second bone anchoring device. The second bone anchoring device may be configured to extend through the first bone, through the spacing member bore, and through the second bone along a trajectory non-parallel to the first bone anchoring device to provide additional compression between the first exterior bone surface and the second exterior bone surface.

The first bone anchoring device may include a first elongated structure and a second elongated structure. The first elongated structure may be coaxially received by the second elongated structure and selectively adjustable relative to the second elongated structure to increase or decrease a distance between first end and the second end to provide a selected level of compression between the first exterior bone surface and the second exterior bone surface.

The spacing member may include a first bone contacting surface and a second bone contacting surface. At least one of the first and second bone contacting surfaces may include a plurality of bone engagement features projecting from the bone contacting surface. The spacing member may be configured to fit into a gap between the first bone and the second bone, the gap bounded by a first face of the first bone and a second face of the second bone. The spacing member may be contoured to conform to the first face of the first bone and the second face of the second bone.

The spacing member peripheral body wall may include a medial portion and a lateral portion. A height of the medial portion may be unequal to a height of the lateral portion to provide a deformity correction when the spacing member is inserted between the first bone and the second bone. The spacing member may be shaped to be inserted into a tibial osteotomy between a tibia and a talus.

The spacing member may further include a flange protruding from a portion of the peripheral body wall. The bone support implant system may further include at least one fastener configured to fasten the flange to one of the first bone and second bones.

The bone support implant system may further include a cortical washer having a rim shaped to bear congruently against the first exterior bone surface and a bore configured to retain the first end of the first bone anchoring device.

The second end of the first bone anchoring device may further include an anchor member. The anchor member may be movable between an insertion configuration and a deployed configuration. In the deployed configuration the anchor member may be configured to bear against the second exterior bone surface on the second bone.

A method of implanting a bone support implant system for providing stabilizing support between a first bone and a second bone may include inserting a spacing member into a space between the first bone and the second bone, the spacing member comprising a peripheral body wall and a bore extending therethrough. The method may further include inserting a first bone anchoring device to extend through the first bone, through the spacing member bore, and through the second bone, attaching a first end of the first bone anchoring device to a first exterior bone surface on the first bone; and attaching a second end of the first bone anchoring device to a second exterior bone surface on the second bone.

Inserting the first bone anchoring device may include inserting the first bone anchoring device along a single straight first trajectory that passes through the first bone, the spacer, and the second bone. The method may further include inserting a second bone anchoring device to extend through the first bone, through the spacing member bore, and through the second bone, along a single straight second trajectory non-parallel to the first trajectory.

The method may further include selectively adjusting the length of the first bone anchoring device to increase or decrease a distance between the first end and the second end to provide a selected level of compression between the first exterior bone surface and the second exterior bone surface.

The first bone anchoring device may further include a first elongated structure and a second elongated structure. The method may further include coaxially receiving the first elongated structure within the second elongated structure, and moving the first elongated structure relative to the second elongated structure to adjust the length of the first bone anchoring device.

The method may further include preparing a tibial osteotomy on the distal end of a tibia and inserting the spacing member into the tibial osteotomy between the tibia and the talus.

The method may further include inserting a cortical washer into an opening in the first bone such that a rim of the cortical washer bears against the first exterior bone surface on the first bone, and retaining the first end of the first bone anchoring device with the cortical washer.

The method may further include moving an anchor member attached to the second end of the first bone anchoring device to a deployed configuration in which the anchor member bears against the second exterior bone surface on the second bone.

The method may further include fastening a flange which protrudes from a portion of the peripheral body wall to at least one of the first and second bones.

Yet another embodiment of the invention may include a modular orthopedic arthroplasty system for controlling relative motion between a first bone and a second bone. The modular orthopedic arthroplasty system may include first and second anchor members, first and second elongated structures, and a mobility structure. The first anchor member may be shaped to bear against a first exterior bone surface on the first bone. The second anchor member may be shaped to bear against a second exterior bone surface on the second bone. The first elongated structure may have a first end and a second end, the first end attachable to the first anchor member. The second elongated structure may have a first end and a second end, the second end attachable to the second anchor member. The mobility structure may be positioned between the first elongated structure and the second elongated structure to allow relative motion between the first bone and the second bone.

The mobility structure may further include a first bearing body, a first bearing surface, a second bearing body and a second bearing surface. The first bearing body may be removably coupled to the first elongated structure and the second bearing body may be removably coupled to the second elongated structure. The second bearing surface may be shaped to bear against the first bearing surface to allow articulating relative motion between the first and second bearing surfaces. The first elongated structure may include a first bolt and a first sleeve. The first bolt may be coaxially received in the first sleeve, and the first bolt may be selectively movable relative to the first sleeve to increase or decrease a distance between the first anchor member and the first bearing surface. The second elongated structure may include a second bolt and a second sleeve. The second bolt may be coaxially received in the second sleeve, and the second bolt may be selectively movable relative to the second sleeve to increase or decrease a distance between the second anchor member and the second bearing surface. The system may further include a bearing insert shaped to be inserted between the first bearing body and the second bearing body. The bearing insert may include one of the first bearing surface and the second bearing surfaces.

The first anchor member may be shaped to bear congruently against the exterior surface of a tibia. The second anchor member may be shaped bear congruently against the inferior surface of a talus. The mobility structure may be shaped to be inserted into a space between the tibia and the talus.

The second anchor member may have an insertion configuration and a deployed configuration. The second anchor member may be selectively movable between the insertion configuration and the deployed configuration. In the deployed configuration the second anchor member may be positioned to bear against the second exterior bone surface.

The modular orthopedic arthroplasty system may further include a third elongated structure. The third elongated structure may be configured to extend between the first exterior bone surface and the second anchor member to substantially prevent relative motion between the first bone and the second bone.

The modular orthopedic arthroplasty system may further include a spacing member having a peripheral body wall and a bore extending therethrough. The spacing member may be shaped to be inserted between the first bone and the second bone to provide load-bearing support between the first bone and the second bone.

A method for implanting a modular orthopedic arthroplasty system may include extending a first elongated structure through a first bone, the first elongated structure having a first end and a second end, the first end attached to a first anchor member. The method may further include positioning the first anchor member to bear against a first exterior bone surface on the first bone and retain the first elongated structure in the first bone. The method may further include extending a second elongated structure through a second bone, the second elongated structure having a first end and a second end, the second end attached to a second anchor member. The method may further include positioning the second anchor member to bear against a second exterior bone surface on the second bone. The method may further include positioning a mobility structure between the first elongated structure and the second elongated structure, the mobility structure allowing relative motion between the first bone and the second bone. The method may further include attaching the mobility structure to the first elongated structure and the second elongated structure.

The mobility structure may further include a first bearing body, a first bearing surface, a second bearing body, and a second bearing surface. The method may further include removably coupling the first bearing body to the first elongated structure and removably coupling the second bearing body to the second elongated structure.

The method may further include adjusting a length of the first elongated structure to increase or decrease a distance between the first anchor member and the first bearing surface. The method may further include adjusting a length of the second elongated structure to increase or decrease a distance between the second anchor member and the second bearing surface.

The elongated structure may include a first bolt received coaxially in a first sleeve. The method may further include adjusting the length of the first elongated structure by moving the first bolt relative to the first sleeve.

The method may further include inserting a bearing insert between the first bearing body and the second bearing body. The bearing insert may include one of the first bearing surface and the second bearing surface.

The method may further include placing the first bone and the second bone in a preferred orientation relative to one another and creating a straight elongated bore extending through the first bone and the second bone along a single trajectory oblique to the intramedullary canal of the first bone. Extending the first elongated structure through the first bone may include inserting the first elongated structure into the straight elongated bore. Extending the second elongated structure through the second bone may include inserting the second elongated structure into the straight elongated bore. Extending the first elongated structure through the first bone may include extending the first elongated structure through a tibia. Extending the second elongated structure through the second bone may include extending the second elongated structure through a talus. Positioning the mobility structure between the first elongated structure and the second elongated structure may include inserting the mobility structure into a space between the tibia and the talus.

The method may further include removing the mobility structure from between the first elongated structure and the second elongated structure, extending a third elongated structure through the first bone and the second bone, and attaching the third elongate structure to the second elongated structure to substantially prevent relative motion between the first bone and the second bone.

The method may further include inserting a spacing member between the first bone and the second bone, and extending the third elongated structure through the first bone, through the spacing member, and through the second bone.

FIG. 1 illustrates an antero-lateral view of the skeleton of a left foot, ankle and distal leg portion. The distal leg portion includes tibia 2 and fibula 4. The bones of the ankle and foot include: talus 6, calcaneus 8, navicular 10, cuboid 12, cuneiforms 14, metatarsals 16, and phalanges 18. The sinus tarsi 20 is a canal-like space formed between the inferior surface of the talus at the sulcus tali and the superior surface of the calcaneus at the calcaneal sulcus.

Figure 2:
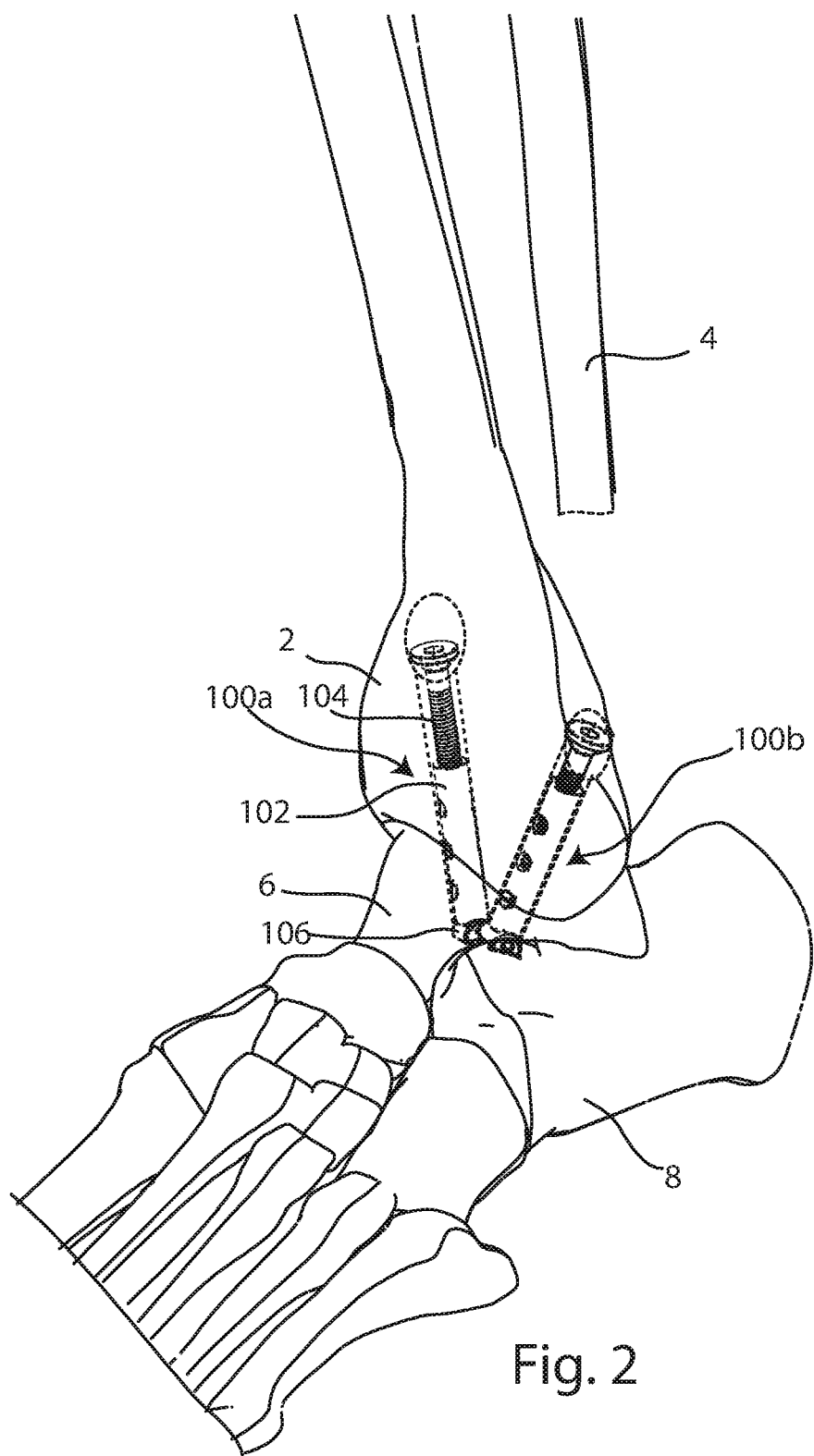
In FIGS. 2, 9, 14, 15, 16, 17, 19, 23, 24, 30, 31, 33, 35, 36 and 37 bone portions surrounding implanted objects are rendered as transparent in order to better view the objects and their positioning within the bone portions.

In at least one embodiment, the present invention provides an ankle arthrodesis system which provides compression across the tibio-talar joint to promote improved bone fusion and joint stability. Referring to FIG. 2, two individual compression systems 100 are shown implanted across a tibio-talar joint, each extending along an oblique trajectory from the an outer surface of the tibia, through the talus, and terminating in the sinus tarsi. A portion of the fibula 4 is not shown in order to better view the implanted systems. Each compression system 100 includes standoff 102, compression bolt 104, and compression nut 106. The compression system 100 and alternative embodiments disclosed herein may be referred to as a compression bolt system, a bone anchoring system or device, or a bone fixation device.

FIG. 2 illustrates an embodiment of a bone fixation system in which two bone anchor systems 100a, 100b are implanted across the same tibiotalar joint. Bone anchor system 100a is installed in a prepared bone bore which extends along a single trajectory between an outer surface of the tibia and an outer surface of the talus, in the sinus tarsi. A portion of the fibula is not shown in order to view the implants more clearly. The addition of a second bone anchor system 100b, implanted in a second prepared bone bore along a single trajectory at an angle oblique to the first system, provides additional stability, compression and fixation across the joint. Implanting two systems at oblique angles may provide cross-fixation to prevent any potential rotation, leading to loosening, about the axis of a single system.

Figure 3A:
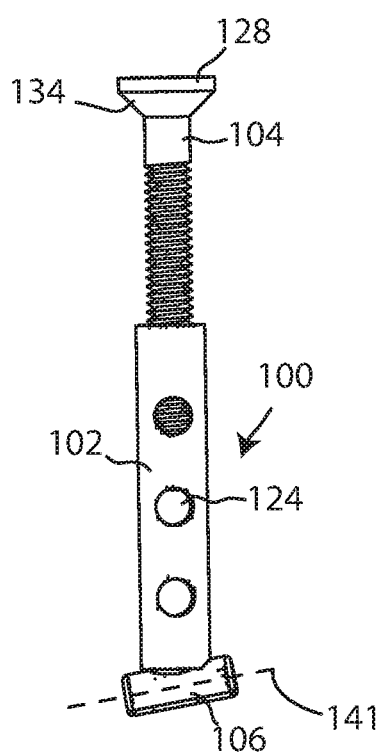
FIG. 3A illustrates the assembled compression bolt system of FIG. 2, the system including a nut, a standoff, and a compression bolt.
Figure 3B:
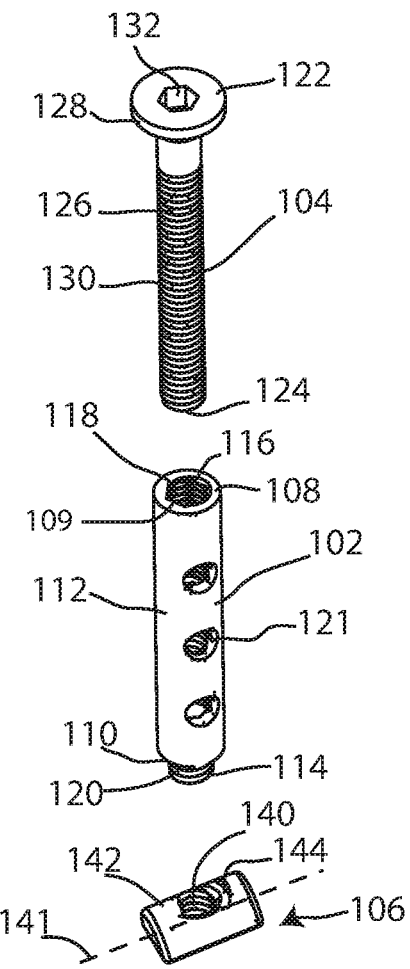
FIG. 3B is an exploded view of the compression bolt system of FIG. 3A.

FIGS. 3A and 3B display compression system 100 in an assembled and an exploded configuration. Standoff 102 is an elongated structure having a first end 108, a second end 110, and a body 112 extending therebetween. At the first end, a driver engagement feature 109 is shaped to engage a driver or other instrument used in implanting and the standoff. A standoff tip 114 projects from the second end 110. Depending on the implanted orientation of the system, the first end 108 may be a proximal end and the second end 110 may be a distal end. The standoff 102 is at least partially cannulated, having a lumen 116 extending from an opening at the first end 108 along some or all of the length of the standoff. The standoff 102 is internally threaded, with internal threads 118 extending the length of the standoff or at least a portion adjacent the first end 108. The standoff tip 114, which may also be called a hub, includes external threads 120. A plurality of openings 121 may be located along the standoff body 112, and may be aligned in pairs such that two openings 121 are positioned opposite one another along the standoff body 112, either directly across from one another or at an oblique angle. The openings 121 may allow bony ingrowth into the standoff once implanted, and may also receive additional bolts or screws for further stabilization of the device. Other embodiments of the standoff may lack openings 121.

Compression bolt 104 is an elongated structure including a first end 122 which may be a proximal end, a second end 124 which may be a distal end, and a bolt body 126 extending therebetween. The bolt body 126 further includes a head 128 at the first end 122, and a threaded shaft 130. The threaded shaft 130 is sized to be received in the standoff lumen 116, and the threaded shaft 130 is threadably engageable with the standoff internal threads 118. The head 128 may include a driving feature 132 which is shaped to connect with a driver and may be formed as a hexagon, star, square, triangle, or rectangle, among others. A bearing surface 134 is formed on the head, and in at least one embodiment is formed on the underside of the head adjacent to where it joins to the shaft. When the system 100 is implanted across a tibio-talar joint and compression bolt 104 tightened, bearing surface 134 bears against the strong cortical bone of the tibia and compression is provided between the head 128 and the compression nut 106, which is anchored against the inferior talar surface in the sinus tarsi.

Figure 3C:
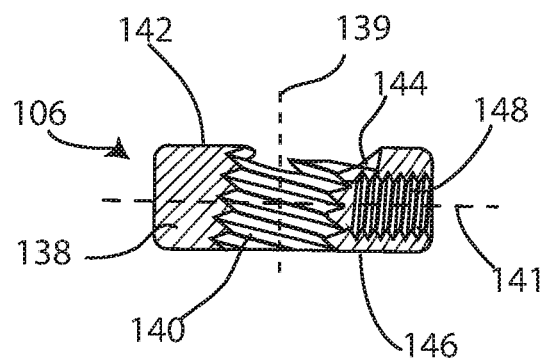
FIG. 3C is a transverse cross-sectional view of the nut of FIG. 3A.

Compression nut 106, which may also be called an anchor member, is seen in cross-section in FIG. 3C and includes a nut body 138 having a vertical axis 139 and a transverse axis 141. A threaded opening 140 extends partially or entirely through the nut body. Threaded opening 140 is a connection feature sized to receive the threaded standoff tip 114, and may be positioned perpendicular or oblique to the transverse axis 141 of the nut body. When attached to the standoff, the transverse axis of the nut may be at an oblique angle relative to the longitudinal axis of the standoff, as seen in FIG. 3A. Oblique positioning of the threaded opening 140 may allow the compression nut to better conform to the irregular shape of the talus, thence providing a firm seating for the nut against the talus. The compression nut 106 further includes a bearing surface 142 which bears against the talus when the bolt 102 is tightened and the system 100 is compressed. Bearing surface 142 may be rounded, or may be flattened, or any other shape which provides desired surface contact with the talus or other bone. For example, as seen in FIGS. 3A-3C, bearing surface 142 may be convexly curved in the form of a partial cylinder to bear congruently against the bone surface, such as the inferior side of the talus in the sinus tarsi. In some embodiments including obliquely threaded embodiments, a recess 144 is located adjacent the threaded opening 140 to provide space for the second end 110 of the standoff when the standoff is tightened or locked onto the nut. On the obverse side of the nut from the bearing surface 142 is a base surface 146, which is shaped to avoid destructive contact with neighboring bone structures such as the calcaneus. Base surface 146 may be flat as in FIG. 3C, or concavely or convexly curved as desired to fit into the anatomical environment. In some embodiments, a second opening 148 is a guide connection feature, providing a means for connection to a guidance instrument. Second opening 148 may be threaded or include recesses or other shaping which connects with a guide arm or other guidance instrument. In alternative embodiments of the invention, the standoff may include the threaded opening, or female connector, while the nut may include the projecting tip, or male connector.

In use, the standoff 102 is threadably connected to the compression nut 106 to form an anchor at the second end of the standoff. The bolt 104 is threaded into the first end of the standoff and selectively tightened to increase or decrease the distance between the head and the nut to provide a selected level of compression between the bolt head and the compression nut, or anchor. This construct may provide an advantage over a simple nut and bolt configuration because inclusion of the standoff allows for the variability in length necessary to achieve the compression. In addition, the variable length allows the device to fit in a wide range of patient anatomies.

Figure 4A:
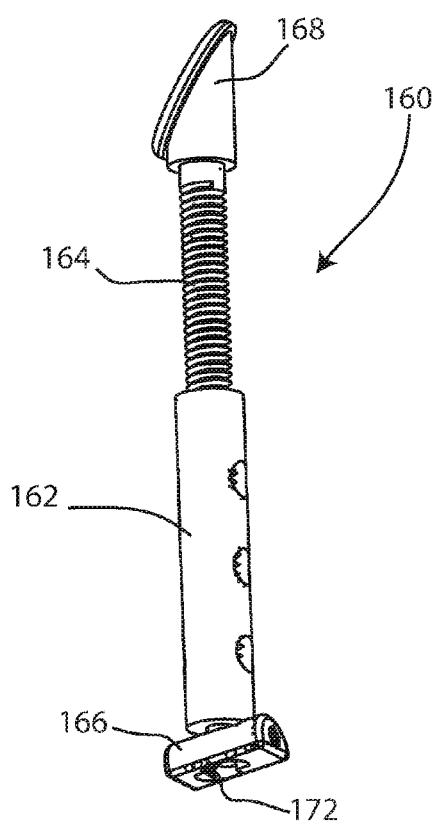
FIG. 4A illustrates a compression bolt system with a T-shaped nut connection.
Figure 4B:
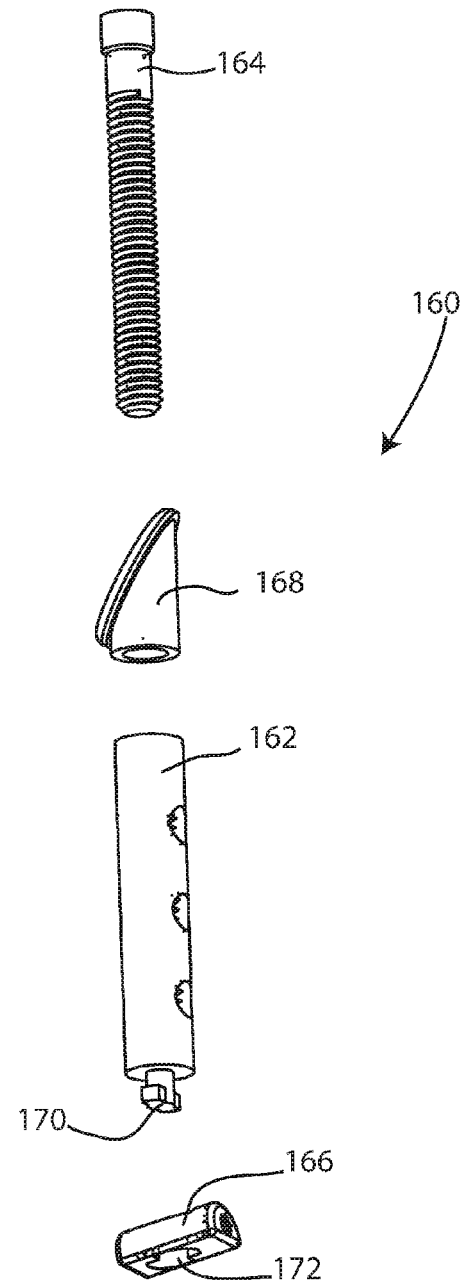
FIG. 4B is an exploded view of the system of FIG. 4A, the system including a nut, a standoff, a compression bolt, and a cortical washer.
Figure 7:
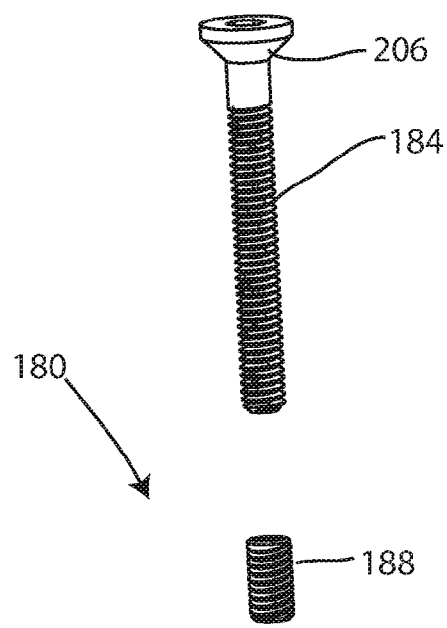
FIG. 7 illustrates the standoff and tabs of FIG. 6, the tabs in an insertion configuration.
Figure 7:
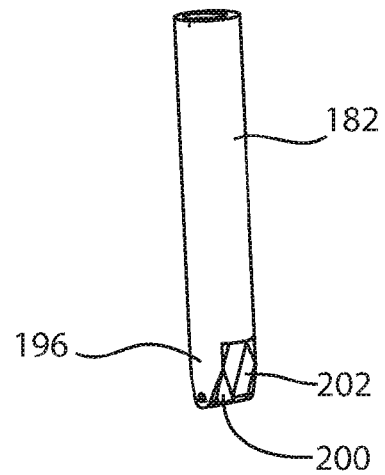
Figure 6:
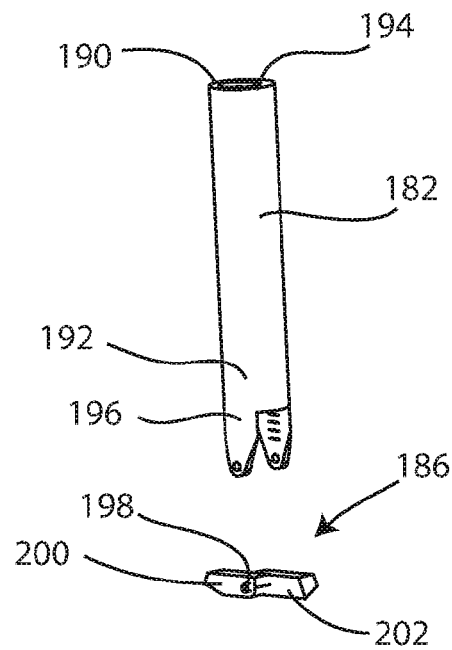
FIG. 6 is an exploded view of a compression bolt system including an anchor including two rotatable tabs, a standoff, a set screw, and a compression bolt.

Referring to FIGS. 4A and 4B, an alternative embodiment of the compression system is shown an assembled and exploded views. Compression system 160 includes standoff 162, compression bolt 164, compression nut 166, and cortical washer 168. Standoff 162 may share many of the features of standoff 102, with at least the exception of standoff tip 170, which is shaped as a T. Compression nut 166 is formed similarly to compression nut 106, except that nut 166 includes keyway 172, which is shaped to receive standoff tip 170. Standoff 162 lockably connects to compression nut 166 by inserting standoff tip 170 into keyway 172, and turning the standoff 162 one-quarter turn relative to the compression nut 166. It is appreciated that alternative embodiments of the system may include standoff-nut connections that require more or less than one-quarter turn to lock together. It is further appreciated that other standoff-nut connections are contemplated within the scope of the invention, including but not limited to threaded connections, snap fit connections, quarter-turn connections, and other keyed connections.

In any of the embodiments disclosed herein, a cortical washer 168 may be included as part of the compression system. Referring to FIG. 5, cortical washer 168 is generally funnel-like or graduated, having a first exterior opening 210 which is greater in diameter than a second interior opening 212. A washer body 214 including a washer bore 216 extends between the two openings, the bore constricted by an internal shoulder 218. The shoulder 218 is sized to retain the head of a compression bolt such as compression bolt 164. The first exterior opening 210 is encircled by a rim 220 which projects laterally from the opening. The inferior surface of the rim 220 includes a rim bearing surface 222, which may be compressed against a bone surface during use. The first exterior opening 210 and surrounding rim 220 may be elliptical as in FIG. 4a, or in other embodiments may be circular, oval, square, hexagonal, rectangular or another shape. The rim bearing surface 222 may be curved or otherwise shaped to fit congruently against the cortical bone surface to which it is fixed. Additionally, the first exterior opening 210 and rim 220 may be positioned oblique relative to the washer bore 216 as in the illustrated embodiment, or perpendicular in alternate embodiments. In this and other embodiments, the exterior of washer 168 may include threads, fins, porous coatings, surface treatments, apertures or other bone-engaging features to assist in engagement with the surrounding bone.

Cortical washer 168 may be placed in the opening on the tibial surface such that its rim sits on the cortical shell of the tibia, and the compression bolt is inserted into the washer, wherein the washer retains the bolt head. Or, alternatively, the compression bolt may be first inserted into the washer followed by placement of the washer into the opening as the bolt is inserted into the standoff. The rim of the washer distributes the compressive load of the bolt head across a greater surface area of the tibial surface than would the bolt head alone. In some instances, the washer also may provide a lower profile between the tibia and the surrounding tissues than would the bolt head alone, as the bolt head is recessed in the washer and only the flat rim of the washer protrudes above the surface of the tibia.

Another alternative embodiment of a compression system is shown in FIGS. 6-11, which depict bolt and standoff combinations including toggle-type anchors at one end. Referring specifically to FIGS. 6-9, compression system 180 is shown in an exploded view, in a retracted or insertion configuration, a deployed configuration, and implanted across a tibotalar joint in a compressed configuration. Compression system 180 includes standoff 182, compression bolt 184, toggle mechanism 186, and set screw 188. Standoff 182 includes a first end 190, a second end 192, and a threaded bore 194 extending therebetween. A pair of standoff extensions 196 projects longitudinally from the second end 192, and a pin 198 extends between the standoff extensions to form a pivot point for the toggle 186. Toggle 186 includes first and second tabs 200, 202 which are pivotable about the pin 198. In the insertion configuration seen in FIG. 7, the tabs are pivoted so that both point toward the first end 190 of the standoff. The tabs 200, 202 are sized and shaped so that when in the insertion configuration, they do not protrude farther than the diameter of the standoff, allowing for smooth unimpeded insertion of the standoff through the tibia; in this configuration the tabs cannot catch or snag on the tibia during insertion. Shaping features of the tabs may include beveling or rounding of the tab ends.

Figure 8:
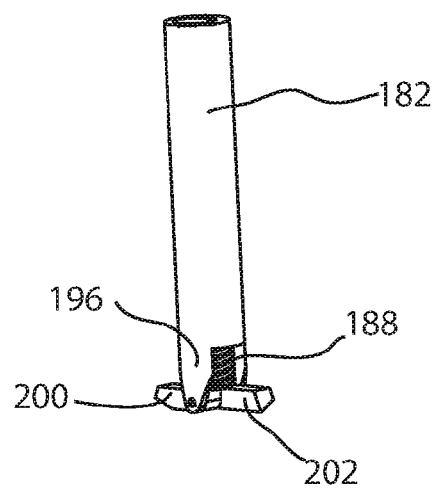
FIG. 8 illustrates the standoff, set screw and tabs of FIG. 6, the tabs in a deployed configuration.
Figure 9:
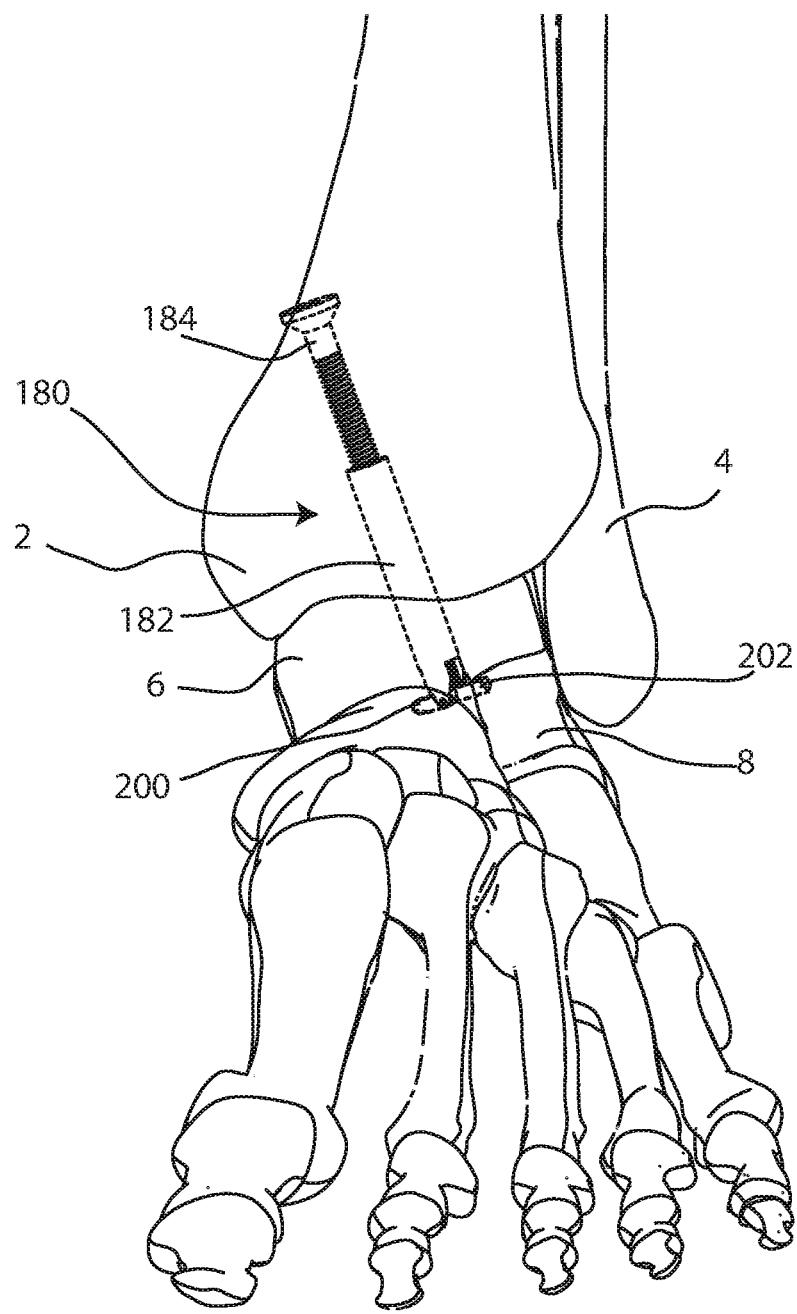

The set screw 188 is sized to be received in the threaded bore 194 of the standoff, and may be already threaded into the bore 194 as the standoff is inserted. Once the standoff is properly positioned in the tibia, the set screw 188 may be turned until it emerges distally from the second end 192 of the standoff, contacts the tabs 200, 202 and pivots the tabs into the deployed configuration, in which the tabs project approximately perpendicular relative to the standoff. In this locked, deployed configuration, the standoff and tabs may form an anchor shape or T shape as seen in FIG. 8. In other embodiments, in the deployed configuration, the tabs may project at an oblique angle, or may partially pivot to form a V shape.

Compression is achieved by threading the compression bolt 184 into the standoff 182 until contact between a bolt head bearing surface 206 bears against the tibia. Continued threading of the compression bolt 184 into the standoff draws the standoff toward the bolt head, or proximally, until the toggle 186 is seated against the lower surface of the talus at a selected pressure, illustrated in FIG. 9. In this embodiment, each tab 200, 202 provides a bearing surface which bear against the talus in the compressed configuration. As with other embodiments of the compression system, a cortical washer may be inserted between the bolt head and the tibial opening. It is appreciated that in this embodiment of the invention, the deployment of the toggle and the compression of the system are carried out by separate actions. Engagement of the set screw with the toggle tabs deploys the toggle, while engagement of the bolt in the standoff provides the compressive force between the bolt head or cortical washer, and the toggle 186.

Figure 10A:
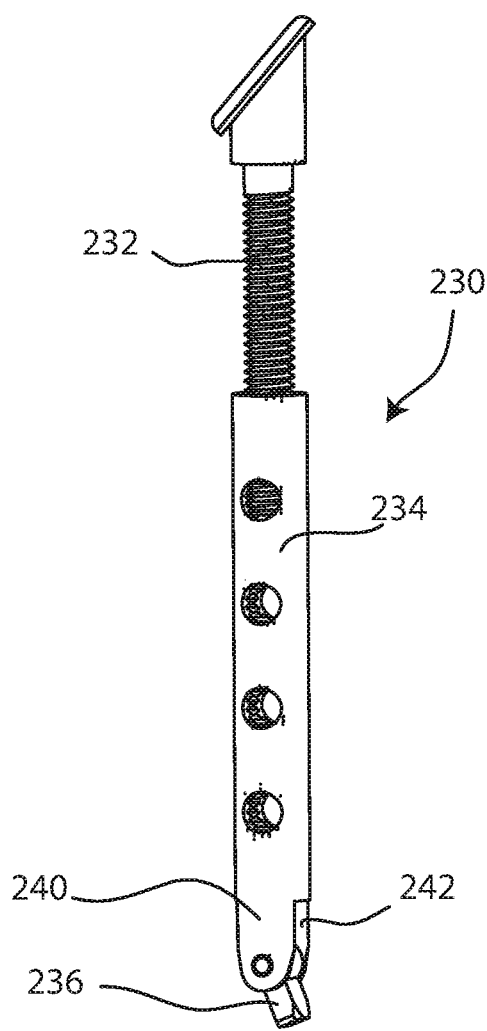
FIG. 10A is an isometric view of a compression bolt system including a single rotatable tab anchor, the anchor in an insertion configuration.
Figure 10B:
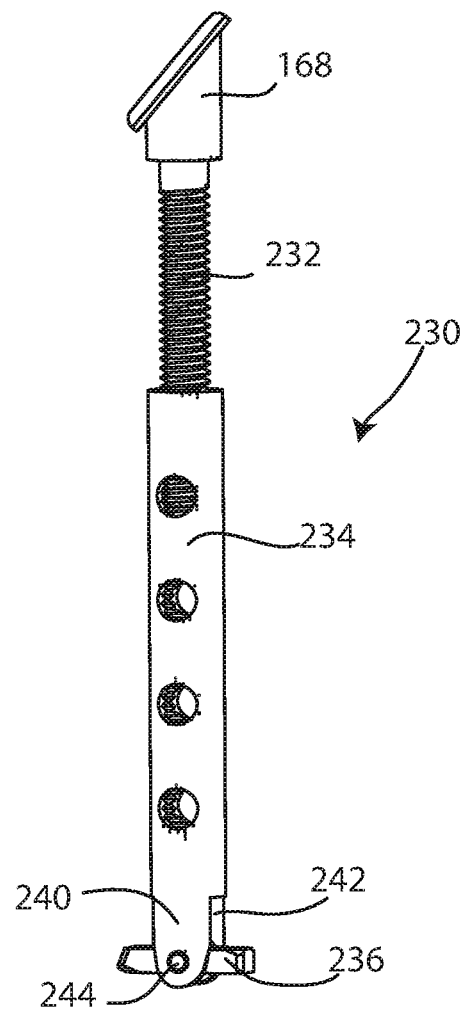
FIG. 10B is an isometric view of the compression bolt system of FIG. 10A with the anchor in a deployed configuration.

FIGS. 10A and 10B illustrate an alternative embodiment of a compression system including a single tab or toggle which actuates by flipping or rotating into a deployed position. Compression system 230 includes standoff 234, compression bolt 232, tab 236, and optional cortical washer 168. Standoff 234 is internally threaded to receive compression bolt 232, and further includes a pair of extensions 240 between which a gap 242 is formed. Tab 236 is rotatably joined to the extensions 240 by a pin 244. The pin 244 provides a pivot point about which tab 236 may rotate, and in rotation a portion of the tab 236 is positioned in the gap 242. In an insertion configuration, illustrated in FIG. 10A, tab 236 is rotated so that it is aligned longitudinally with the standoff 234. In this position, the standoff may be inserted into the prepared reamed hole in the tibia and talus until the standoff extensions 240 protrude into the sinus tarsi. When the standoff is sufficiently inserted so that the tab 236 encounters the calcaneus, contact with the calcaneus may urge rotation of the tab 236 to the deployed position seen in FIG. 10b, in which the tab is approximately perpendicular to the longitudinal axis of the standoff. Advantageously, depending on the shapes of the sinus tarsi and the lower surface of the talus, the tab may assume an oblique angle relative to the longitudinal axis of the standoff when in the deployed position. The compression bolt 232 is threadably engaged in the standoff and turned until a selected level of compression is achieved between the bolt head, or cortical washer 168, and the tab 236. During and after compression the angle of the tab 236 may shift slightly as the tab 236 seats or bears against the talus.

Referring to FIGS. 11A-11D, another alternate embodiment of a compression system or bone anchoring system is shown. Bone anchoring system 250 includes standoff 252, compression bolt 254, a plurality of tabs 256, and set screw 258. The system may further include a cortical washer 168. Standoff 252 is internally threaded to receive compression bolt 254 at a first or proximal end 260, and internally threaded to receive set screw 258 near a second or distal end 262. The tabs 256 are coupled to the standoff 252 near the distal end 262, and each is pivotable between an insertion configuration, seen in FIGS. 11A and 11B, and a deployed configuration seen in FIGS. 11C and 11D. Although FIGS. 11A-1D depict an embodiment with two tabs 256, it is appreciated that other embodiments may include greater numbers of tabs.

Each of the paired tabs 256 is generally L-shaped, having a first leg 264 and a second leg 266. Portions of each leg may include beveled portions 268 which are angled to the major surfaces of the legs. These beveled portions 268 cause the tabs, when in the insertion configuration, to have an outer transverse dimension which is less than or equal to the outer diameter of the standoff, so that the system may be implanted into a bone bore having a diameter equal to or slightly greater than the standoff. During implantation into a prepared bone bore across a joint, the standoff 252 may be inserted into the bone bore in the insertion configuration with set screw 258 already threaded into the standoff lumen but not fully impinging on the tabs 256. The standoff 252 is inserted until the second legs 266 of the tabs 256 have passed through the bone bore and extend past the exterior bone surface. The set screw 258 is actuated until it impinges on the first legs 264 of the tabs 256, pivoting the tabs from the insertion configuration to the deployed configuration, and holding the tabs in the deployed configuration. The compression bolt 254 is inserted in the distal end of the standoff and rotated to decrease the distance between a bolt head 270 and the tabs 256. The bolt head 270, or cortical washer 168 if used, will compress against the exterior bone surface at a first end of the bone bore, and the tabs 256, specifically second legs 266, will compress against the exterior bone surface at a second end of the bone bore. The bolt 254 may be selectively tightened to provide a selected level of compression across the joint.

It is appreciated that the embodiments illustrated in FIGS. 6-11D may be implanted solely through a single opening reamed through the tibia and talus. No additional openings to access the sinus tarsi are required, since in each embodiment the toggle or tabs do not require lateral access or contact to be deployed.

Figure 12:
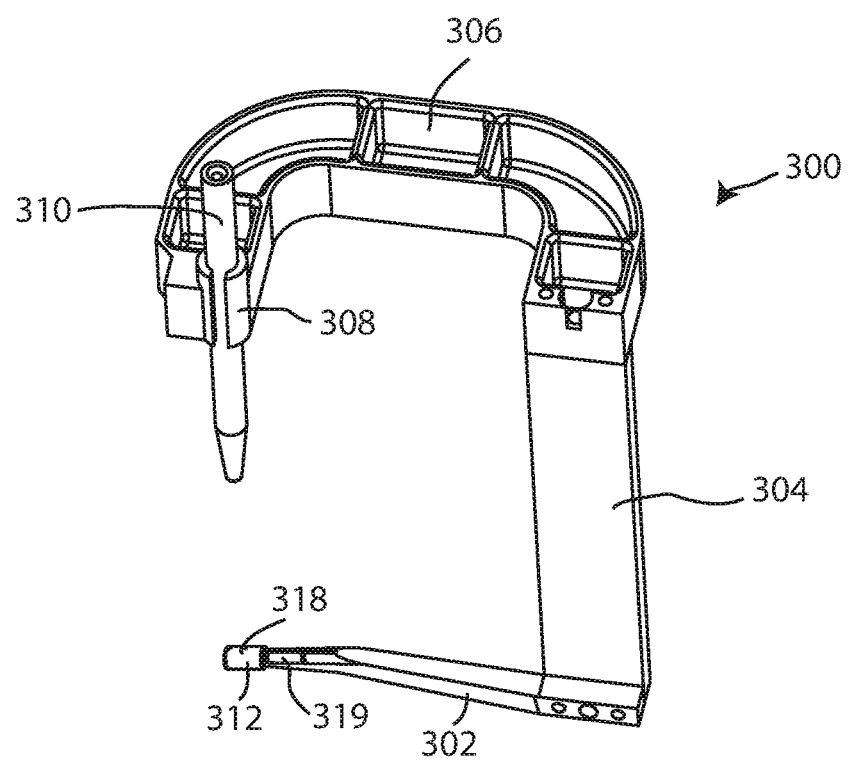
FIG. 12 is an isometric view of a modular targeting guide system including a top arm, upright, targeting guide arm and guide sleeve.

Bone fixation systems described herein, including 100, 100a, 100b, 160, 180, 230, 250 and others may be implanted using a modular targeting guide system 300, as illustrated in FIGS. 12-16. FIG. 12 depicts one configuration of guide system 300, including targeting guide arm 302, upright 304, top arm 306, and guide sleeve 310. Targeting guide arm 302 is removably connectable to upright 304, allowing guide arms of differing lengths, sizes and angles to be used depending on patient anatomy and particular trajectory of the implantation of the bone fixation system. Upright 304 is also removably connected to top arm 306. Top arm 306 is generally U-shaped to allow positioning of the top arm around the patient's leg, although it is appreciated the top arm may include other shapes selected to complement other bone structures or differing patient sizes. Top arm 306 includes a retaining feature 308 which is shaped to hold the generally tubular guide sleeve 310. Targeting guide arm 302 further includes targeting nut 312 having a target point 318. Targeting nut 312 is sized and shaped similarly to nut 106, and may be formed unitarily with the guide arm or may be removable. Guide sleeve 310 is positioned to guide a guide wire along a single selected trajectory to meet a target point 318 on targeting nut 312. A distal end 319 of the guide arm may be shaped to orient targeting nut 312 at a selected angle, which may be oblique, relative to the longitudinal axis of guide sleeve 310.

Figure 13A:
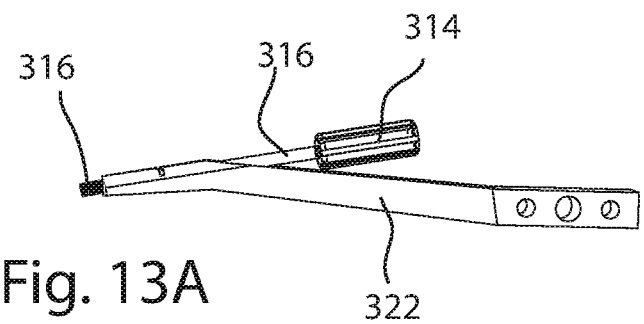
FIG. 13A illustrates an anchor positioning arm attachable to the targeting guide system of FIG. 12.
Figure 13B:
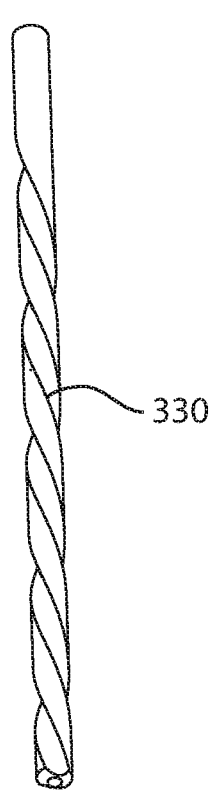
FIG. 13B illustrates a reamer and FIG. 13C illustrates a driver.
Figure 13C:
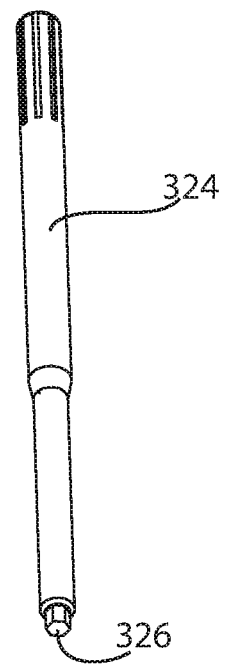

Guide system 300 includes further arms and tools shown in FIGS. 13A-13C, which may be selectively used to perform implant installation actions described herein. FIG. 13A depicts a nut positioning arm 322 including a targeting nut retainer 314 having a threaded shaft 316. FIG. 13B depicts a reamer 330; FIG. 13C depicts a standoff/bolt driver 324 including a driving feature 326. It is also appreciated that guide system 300 may include features for attachment to a surgical table, framework or other platform to provide stability for the framework during surgical procedures utilizing the system.

Figure 14:
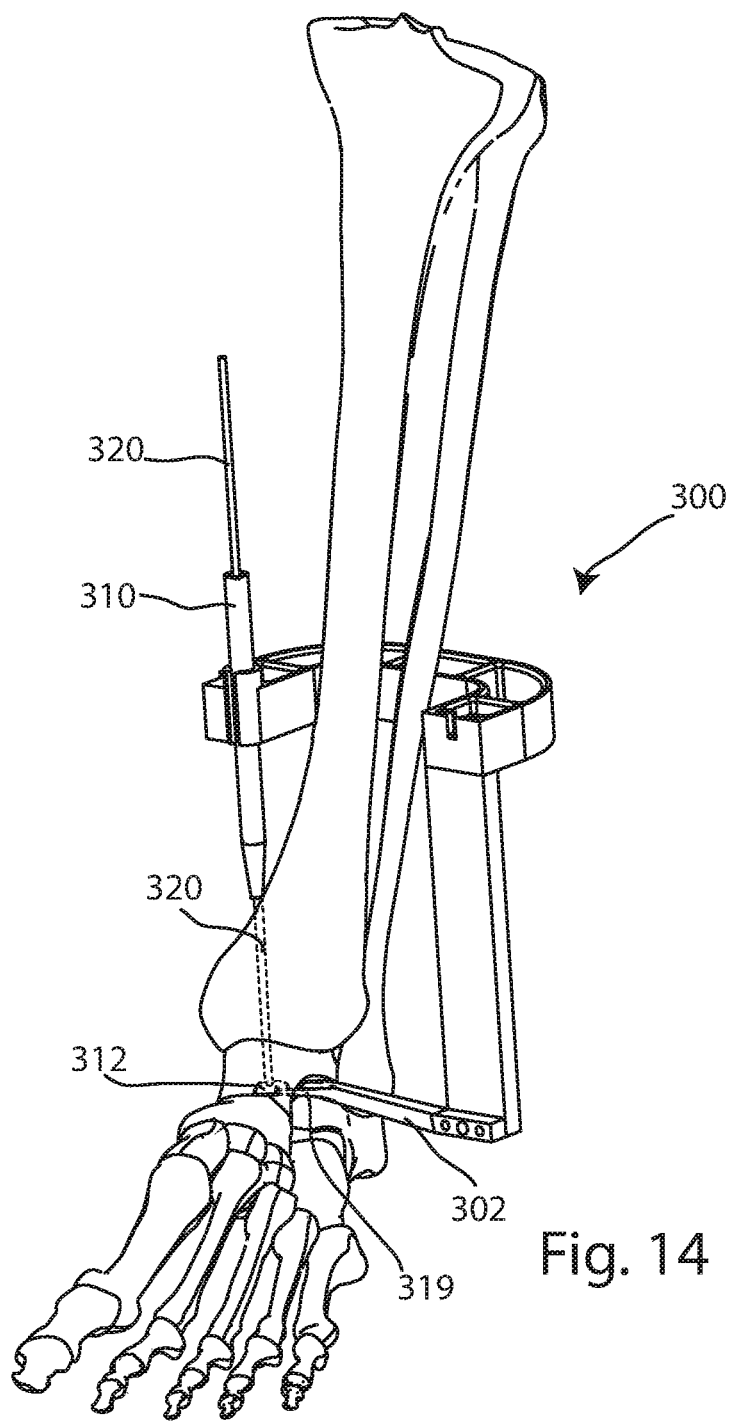

FIG. 14 depicts targeted guide system 300 positioned about the tibia and fibula of a patient's leg with a guide wire 320 distally and laterally inserted through a portion of the tibia. The distal end 319 of targeting guide arm 302 with targeting nut 312 has been inserted into the sinus tarsi, between the talus and the calcaneus. The guide sleeve 310, which may also be termed a drill guide, guides the guide wire 320 to pass along the selected trajectory through the tibia and the talus to meet the target point 318 on the targeting nut 312. Once the guide wire has been inserted through the tibia and talus, guide system 300 may be removed, leaving the guide wire in place. The reamer 330, which may be cannulated to fit over the guidewire, is passed along the selected trajectory to ream a bone bore of a preferred diameter through the tibia and talus along the trajectory. The preferred diameter may be the outer diameter of the standoff of bone fixation system to be implanted.

After the bore is reamed along the selected trajectory, the nut positioning arm 322 may be attached to the guide system 300 in place of the guide arm 302. Nut positioning arm 322 includes targeting nut retainer 314, which has a threaded shaft 316 which extends through a bore in nut positioning arm 322 to removably attach to and retain nut 106 at a distal end 324 of the guide arm. The threaded shaft 316 threadably engages in second opening 148 of the nut 106. It is appreciated that other means may be used to attach compression nut 106 to guide arm 302, such as retaining arms, tongs, threaded connections, and shaped connections, among others. Guide system 300 is positioned adjacent the patient's leg and the distal end of the nut positioning arm 322 with attached nut 106 is positioned with the nut 106 in the sinus tarsi at the opening to the bone bore.

Figure 15:
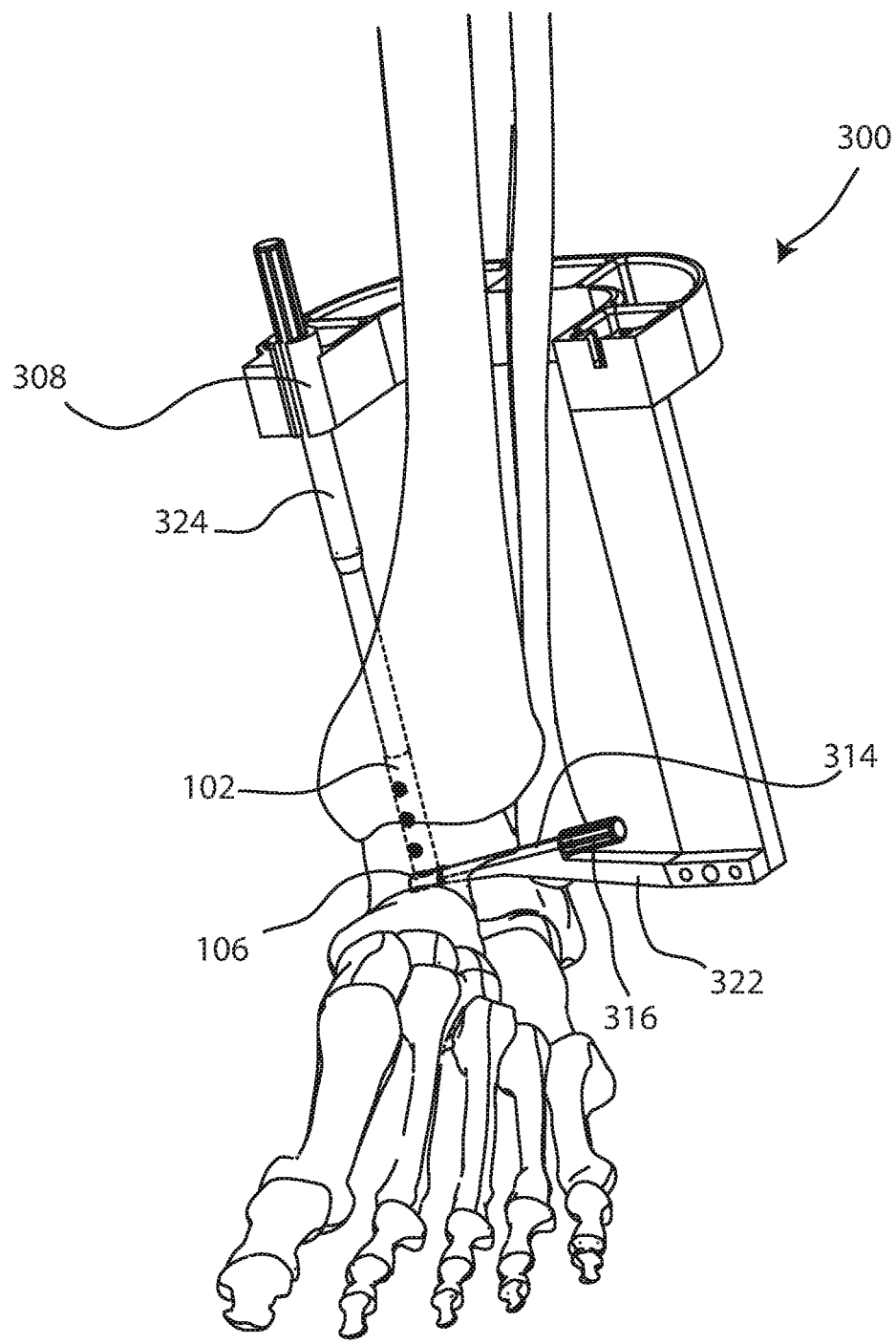

Referring to FIG. 15, standoff 102 is inserted into the reamed bone bore and connected with the compression nut 106. A standoff driver 324, which may be guided through retaining feature 308, rotates the standoff 102 relative to the nut 106 so that standoff tip 114 threadably engages in the threaded opening 140 of the compression nut 106. Thus the nut 106 attains a deployed configuration. The nut positioning arm 322 prevents the nut from rotating during the tightening of the standoff. It is appreciated that for other embodiments of the invention, the standoff may not need to be rotated to engage with or deploy an anchor. The standoff driver 324 includes a driver feature 326 which engages with driver engagement feature 109 on the standoff to rotate the standoff. The driver feature and driver engagement features may be complementarily shaped with a hex connection, square connection, star connection or other connection known in the art to allow the driver to actuate the standoff.

Once the standoff 102 is properly positioned in the bone bore and connected to the compression nut 106, nut positioning arm 322 and guide system 300 may be removed; optionally, it may stay in place and be removed after engagement of the compression bolt 104 with the standoff 102. For removal, threaded shaft 316 of the targeting nut retainer 314 is unthreaded from the compression nut, and the nut positioning arm 322 is withdrawn. The remainder of the implantation may be performed without employing the guide system 300. Compression bolt 104 is inserted into the bone bore and threaded into the standoff internal threads 118. A bolt driver is engaged with the driving feature and actuated to move the bolt relative to the standoff. The bolt driver may be the same instrument as the standoff driver. As the bolt 104 is tightened, the distance between the bolt head 128 and nut 106 decreases as the bolt moves along the standoff lumen 116. Bolt 104 may be tightened until head 128 contacts the exterior bone surface around the bore entrance on the tibia, at which point further tightening may draw standoff 102 and nut 106 toward the head 128, compressing the tibiotalar joint into a fixed relationship and substantially preventing relative motion between the tibia and the talus across the joint.

Figure 16:
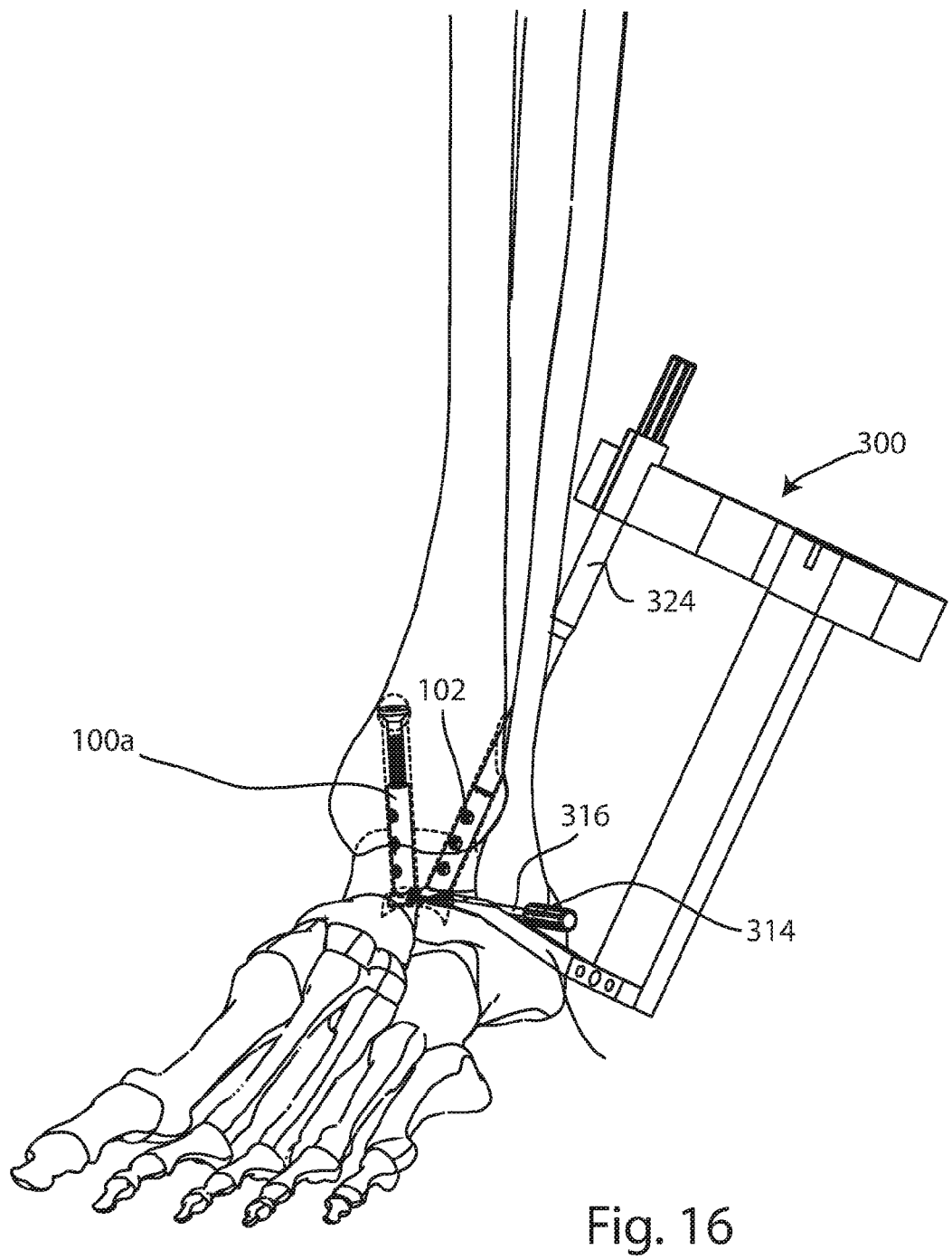

Optionally, a second compression system may be implanted, as shown in FIGS. 2 and 16. The guide system 300 may be repositioned with the targeting nut 312 of the guide arm 102 inserted into the sinus tarsi, the targeting nut 312 adjacent the first implanted compression nut 106. The system 300 is positioned so that guide sleeve 310 will guide the guidewire 320 along a second trajectory which may be non-parallel to the first trajectory and first compression system. The remaining steps are completed as set forth above to insert the guide wire, ream the bone bore, insert the second nut, insert the second standoff and connect to the second nut, and tighten the second bolt into the second standoff.

Other embodiments of the compression system, or bone fixation system may be implanted in a similar manner using some or all the instruments disclosed above. For example, compression system 160 including quarter-turn nut 166 may be implanted using guide system 300. Nut retaining arm 322 may retain quarter-turn nut 166 in the same manner as it retains nut 106. Compression systems 180, 230 and 250 including toggle type anchors may not require use of the nut retaining arm, but the remainder of the guide system 300 may be implemented to position and implant the systems.

Another embodiment of the invention includes a first compression system as set forth herein implanted across a joint to immobilize the joint, plus a screw implanted across the joint along a trajectory different from the trajectory of the first compression system to provide further stabilization. This combination might be utilized in an ankle fusion procedure if it is determined that the sinus tarsi cannot accommodate more than one anchor member.

Figure 17:
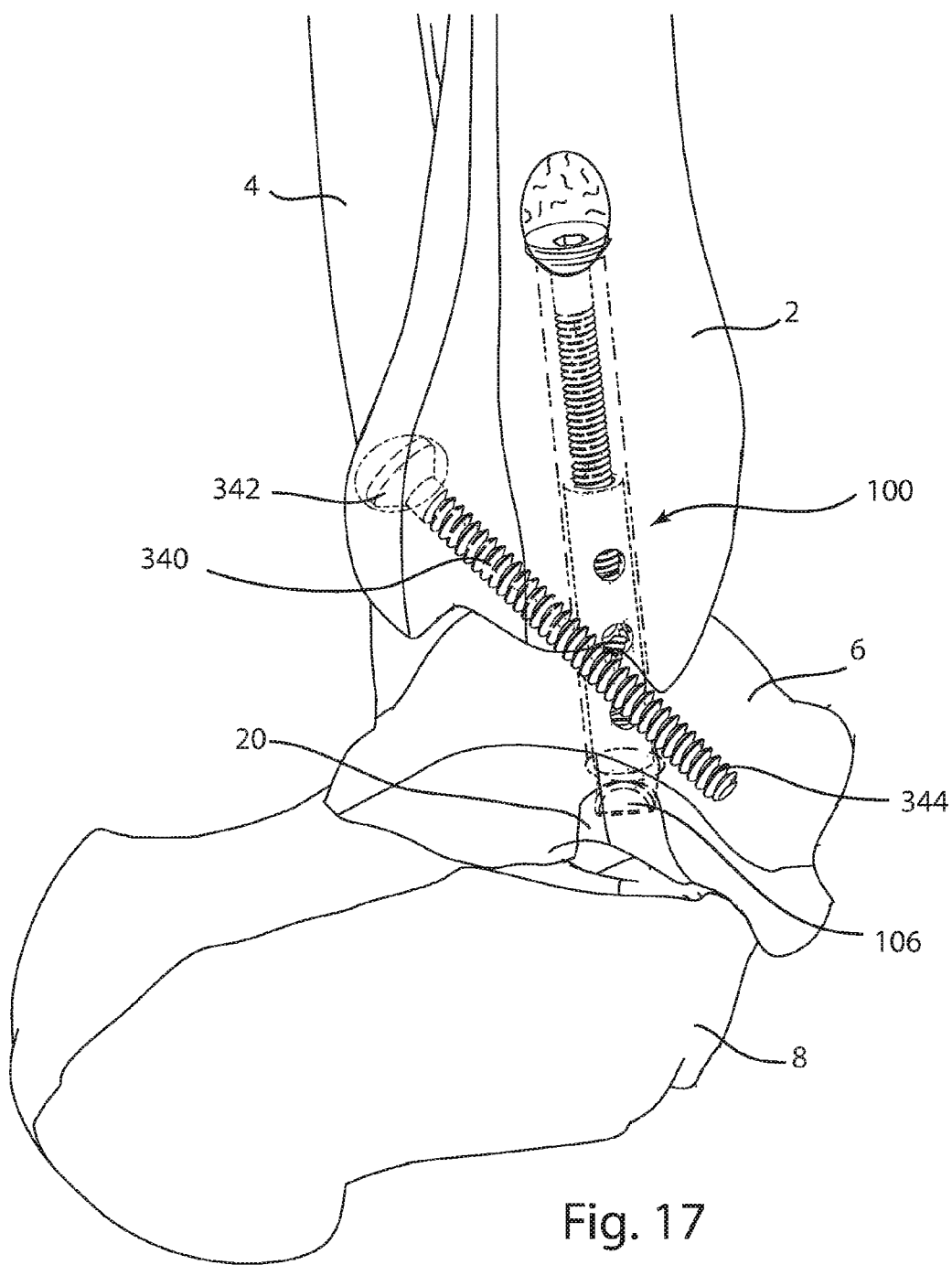

Referring to FIG. 17, an alternate embodiment of a compression bolt system and screw combination is shown. FIG. 17 depicts a medial view of a tibia, talus, and calcaneus with a compression bolt system 100 and a supplementary screw 340 implanted across the tibiotalar joint. A head 342 of screw 340 is positioned at the exterior bone surface of the tibia, and a tip 344 of the screw is lodged within the talus; in this embodiment the screw does not extend entirely across the talus to emerge outside of the talus, unlike the anchoring nut 106 of the compression system 100. In another embodiment, the screw 340 may be implanted to traverse the compressing bolt system 100, passing through two of the openings 121 in the standoff 102. It is appreciated that guide system 300 may be implemented to position and implant screw 340 as well as compression system 100.

Suitable materials for the hardware disclosed herein, including but not limited to compression bolts, standoffs, screws, washers, toggles, tabs, nuts, and anchors, may include any biocompatible metals and metal alloys, including titanium/titanium alloys, stainless steel, cobalt chrome, tantalum, and barium.

During preparation of a tibiotalar joint for fusion it is often necessary to remove significant amounts of cartilage. In this situation, a spacer inserted into the resected area can serve to fill the space, and provide structural load-bearing support and stability to the surrounding environment. In addition, a spacer may help prevent leg length discrepancy, and can provide deformity correction. Such a spacer may be referred to as a bone support implant.

Referring to FIGS. 18A-C, multiple embodiments of a tibiotalar spacer member, or spacer, are shown. Each spacing member may be implanted into a resected tibiotalar joint alone, or in combination with any of the compression bolt systems described herein, the compression bolt system passing through an opening in the spacer member to anchor the spacer member in a desired position. Spacer members may further include openings for screw fixation, and/or anterior or lateral plates for additional stabilization and screw fixation. The spacer geometry can be varied to suit the selected surgical technique, or patient anatomy. For example, a surgeon may prefer to resect the bone surfaces flat to achieve conformance, in which instance a spacer member with flat inferior and superior surfaces may be optimal. In another example, the spacer may need to be tapered or wedge-shaped to accommodate or correct patient anatomy.

FIG. 18A illustrates superior and front views of an anatomic spacing member 400 which is anatomically shaped to congruently fit the superior side of a talus. Spacing member 400 includes a peripheral wall 402 which encircles a generally central graft opening or window 404. The spacing member 400 further includes a superior side 406 and an inferior side 408, a first end 410 and a second end 412. Spacing member 400 is generally arched or curved, the superior side 406 being convexly curved between the first end and the second end, and the obverse inferior side 408 being concavely curved between the first end and the second end. A medial side 418 is opposite a lateral side 416, and the superior 406 and inferior 408 sides are also slightly curved between the medial side and the lateral side. Of course, in other embodiments, the spacing member may be curved in only one aspect and not the other, and/or the superior side may be concavely curved while the inferior side is convexly curved.

FIG. 18B illustrates a box-like or flat spacing member 420, including a peripheral wall 422 and a window 424. Spacing member 420 is flat, with superior and inferior sides spaced evenly apart. However, the perimeter wall 422 and window 424 are irregularly shaped, like those in anatomic spacing member 400, to generally fit the cross-sectional shapes of the tibia and the talus between which it may be implanted.

FIG. 18C illustrates a wedge-shaped deformity correcting spacing member 430, having a peripheral wall 432 and window 434. A superior side 436 is sloped or angled relative to an inferior side 438. A lateral side 440 has a greater height than a medial side 442, as measured from the inferior surface to the superior surface at the respective lateral and medial sides. In other embodiments, the medial side may be taller than the lateral side, or the heights at the first and second ends may differ to provide alternate deformity corrections.

Any of the spacing members disclosed herein may include teeth, keels, ridges, splines, porous coatings, surface roughening, or other features or treatments on any surface to enhance engagement with surrounding structures and prevent migration of the spacing member. As seen in FIG. 18D, a toothed spacing member 450 is anatomically shaped like spacing member 400, and further includes a plurality of teeth 452 arrayed on both the superior and inferior sides. A first section 454 and a second section 456 remain toothless, which may aid in implantation of the spacing member and interaction with adjacent anatomy.

Figure 19:
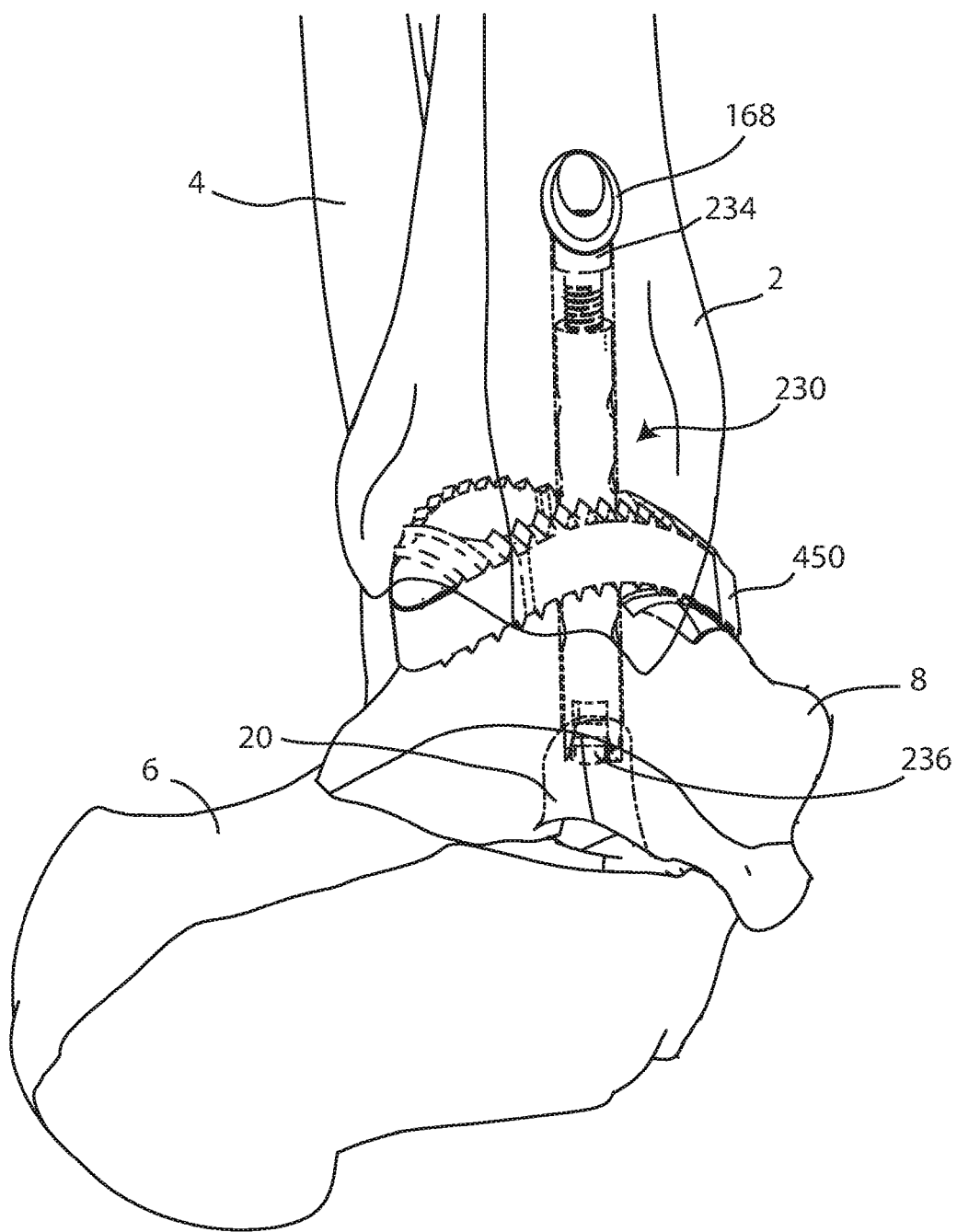

FIG. 19 illustrates a medial view of toothed spacing member 450 implanted in a tibiotalar joint, with a compression bolt system 230 providing additional fixation for the spacing member. Spacing member 450 is positioned to congruently fit on the superior surface of the talus, and fill space between the talus and the tibia. Cortical washer 168 provides an anchor on the exterior bone surface at a proximal end on the tibia, and tab 236 provides an anchor on the exterior bone surface at a distal end on the talus, in the sinus tarsi. The combination of the spacing member and compression bolt system may be referred to as a bone support implant system.

Figure 20A:
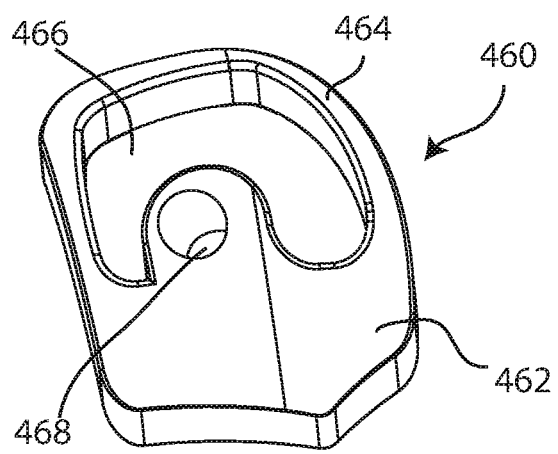
FIG. 20A is an isometric view of an anatomic spacing member including a fixation aperture extending through a spacer body.

FIGS. 20-22 provide additional spacing member embodiments. FIG. 20A illustrates spacing member 460, including spacer body 462, peripheral wall 464, window 466, and fixation aperture 468. Fixation aperture 468 extends between superior and inferior surfaces of the spacer body 462, and is sized to receive a compression bolt system such as system 100, 160, 180, 230 or 250. The aperture may be angled relative to the spacer body to accommodate the proper trajectory for the compression bolt system and standoff. An additional compression bolt system, or a screw, may be implanted to pass through the window 466.

Figure 20B:
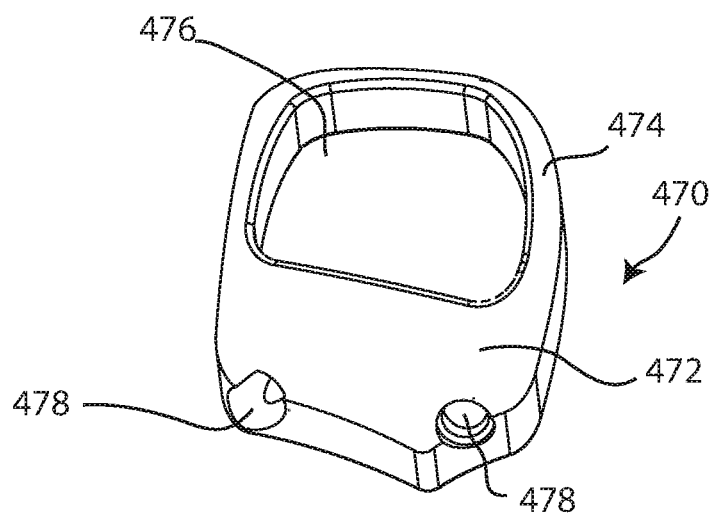
FIG. 20B is an isometric view of an anatomic spacing member including a plurality of fixation apertures extending through a spacer body.

FIG. 20B illustrates spacing member 470, including spacer body 472, peripheral wall 474, and window 476. A plurality of fixation apertures 478 extend through the spacer body and/or the peripheral wall. Fixation apertures 478 are configured to receive bone screws, bolts, or other bone anchors. Each individual fixation aperture 478 may have a different trajectory, angle, or orientation relative to the spacing member in order to provide optimal fixation and stability when fixation members are positioned to extend through the apertures to attach the spacing member to a bone. Each fixation aperture 478 may be graduated or have a tapering diameter through the spacer body or peripheral wall, providing a low profile spacing member system in which the fixation members are recessed into the fixation aperture and do not protrude beyond the exterior surface of the spacing member. Also, each fixation aperture 478 may be threaded to receive a bolt at a preferred trajectory. It is appreciated that a bolt may be driven through a fixation aperture 478 from either a generally anterior to posterior direction, or from a generally posterior to anterior direction. At least one fixation aperture 478 is oriented so that a bolt or screw may be installed from an anterior approach through the aperture without intersecting the adjacent metatarsal, cuneiform and navicular bones.

Referring to FIGS. 21A-C and 22, spacing members including flanges or plates which may provide fixation and/or structural support are illustrated. FIGS. 21A and 21B illustrate an anatomically shaped spacing member 490 which further includes two fixation flanges disposed on the lateral side of the spacing member. Spacing member 490 includes spacer body 492, window 496, and support structure 498. A portion of the spacer body 492 forms a peripheral wall 494 surrounding the window 496. Support structure 498 further includes a first flange 500 and a second flange 502, each flange projecting outwardly at an angle from the spacer body 492. Each flange 500, 502 includes a plurality of fixation apertures 504 sized to receive a fixation member such as a bone screw, bolt, or other bone anchor. The flanges are positioned so that when the spacing body 492 is implanted into the space between a tibia and a talus, fixation members may be secured into the tibia through the apertures 504 in flange 500, and fixation members may be secured into the talus through the apertures 504 in flange 502. It is appreciated that in other embodiments, the flanges may be positioned on the medial, anterior, and/or posterior sides of the spacer body.

Referring to FIG. 21C, a spacing member 510 includes a spacer body 512, first 514 and second flanges 516 disposed on a lateral side of the spacer body, and a third flange 518 disposed on an anterior aspect of the spacer body. A plurality of fixation apertures 520 extend through the flanges 514, 516, 518 and the spacer body 512 to allow placement of multiple fixation members to secure the spacing member to bony structures. It is appreciated that due to patient anatomy, compromised tissues, or surgeon preference, not every fixation aperture must be used in securing the device to the bony structures; some apertures may be left empty if desired.

In another embodiment, a plate member alone may be fixed to the tibia and talus to providing stabilization and/or fusion of the tibiotalar joint. Depicted in FIG. 21D, plate member 522 comprises a first flange 524 and a second flange 526. A plurality of fixation apertures 528 provide openings through the flanges, through which fixation members may pass to secure the plate member to bony structures. The fixation members may be oriented polyaxially in a variety of planes to provide multi-angle cross-fixation. Alternately, the fixation members may be oriented in coplanar arrangement with one another. The angular relationship between the first and second flanges 524, 526 may vary according to patient size, specific anatomy and/or deformity correction as necessary. Plate member 522 may be implanted anteriorly or laterally as needed and can be inserted with minimal exposure.

Figure 22A:
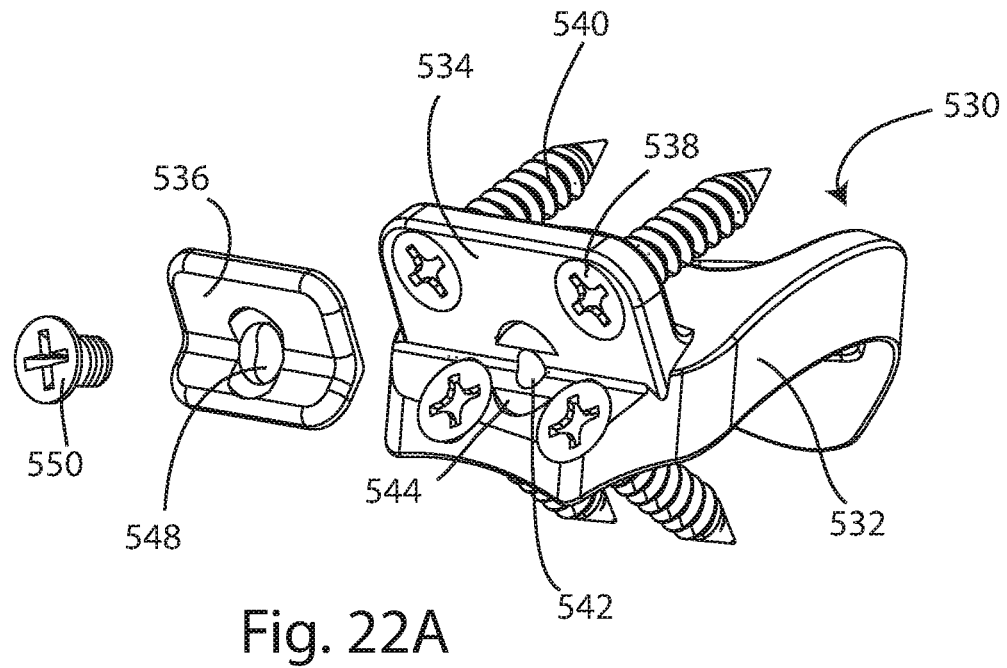
FIG. 22A is an isometric exploded view of a spacing member including an anterior fixation flange, a supplementary plate and a plurality of fixation members.
Figure 22B:
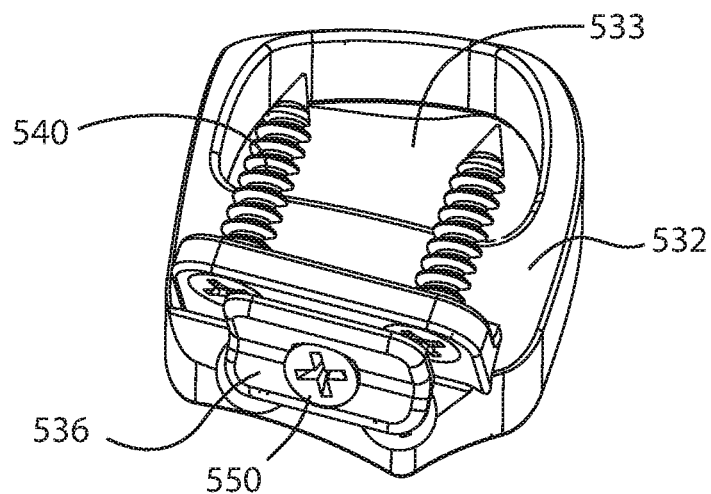
FIG. 22B is an isometric view of the assembled spacing member, supplementary plate and fixation members.

Referring to FIGS. 22A and 22B, a spacing member 530 includes a spacer body 532, window 533, flange 534, supplementary plate 536 and a plurality of fixation members 540. Spacer body 532 and flange 534 each include at least one fixation aperture 538, through which fixation member 540 may pass to secure the spacing member to bony structures. Spacer body 532 further includes retention aperture 542 and an attachment feature 544. Supplementary plate 536 is sized and shaped to fit congruently against an anterior aspect of spacer body 532 and flange 534, such that the plate overlaps a significant portion of each fixation aperture 538. Thus, supplementary plate 536 functions as an anti-backout mechanism, physically preventing fixation members 540 from withdrawing from fixation apertures 538. Supplementary plate 536 further includes retention aperture 548, through which retention member 550 may pass to be secured into retention aperture 542 on the spacing member. An attachment feature 544 may be disposed on spacing member 530 to provide a place for temporary attachment of instruments such as an implant insertion tool, among others.

Figure 23:
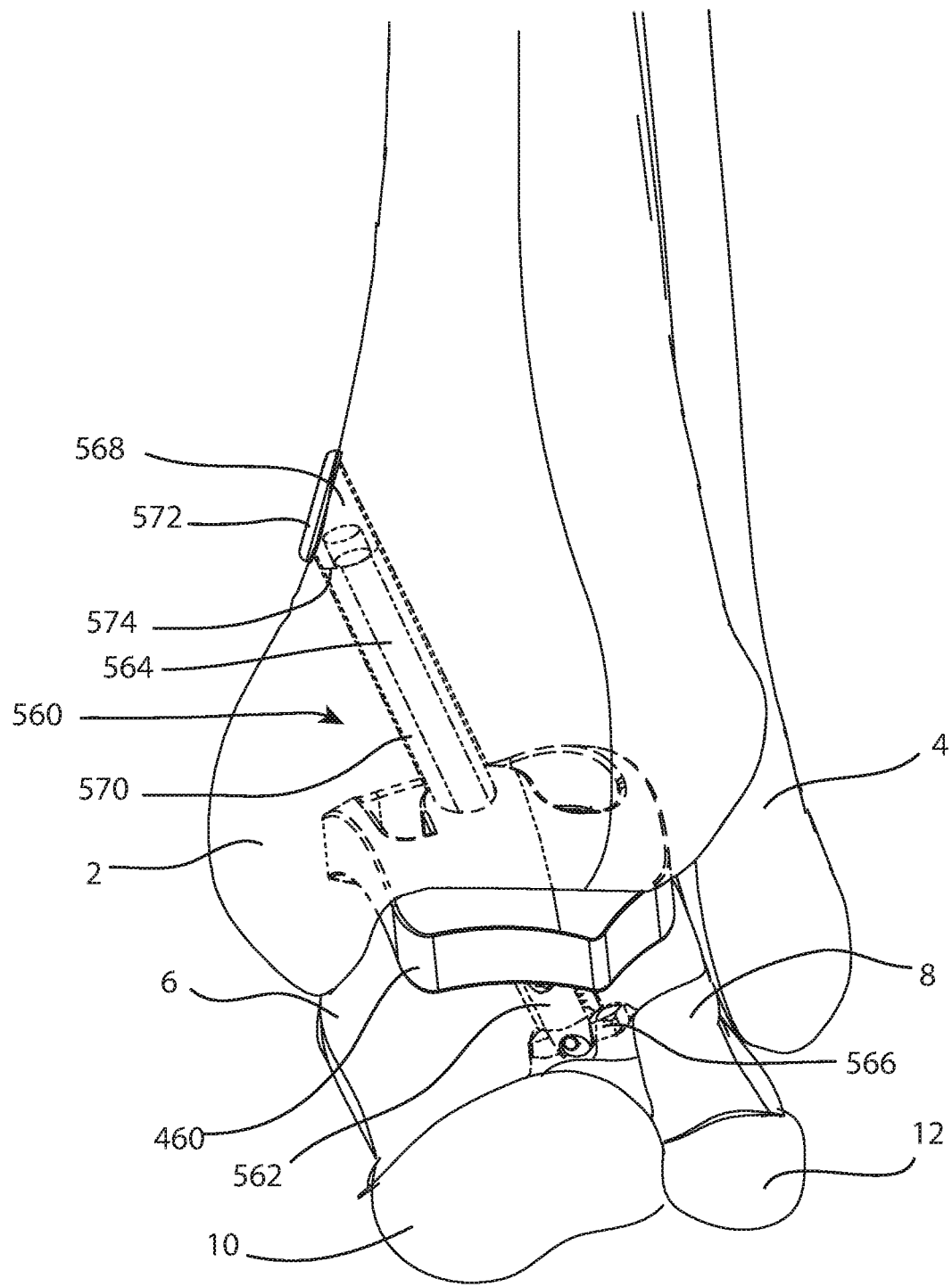

Referring to FIG. 23, an anterior view shows spacing member 460 implanted in a tibiotalar joint, with a compression bolt system 560 passing through the fixation aperture 468, and anchoring the spacing member and compression bolt between first and second exterior bone surfaces on the tibia and the talus. Compression bolt system 560 includes standoff 562, compression bolt 564, tab 566, plus extended cortical washer 568. Standoff 562 may be shorter in length than other standoff disclosed herein, and extended cortical washer 568 may be longer than other cortical washers. Cortical washer 568 includes an elongated tubular body 570, rim 572, and annular shoulder 574 which is shaped to retain the head of the compression bolt 564. The extended length of the cortical washer body 570 may provide protection between the compression bolt 564 and the fixation aperture 468. In another embodiment, the tubular body of the cortical washer may be shorter, and the standoff may be longer, wherein the standoff extends through the fixation aperture 468 when spacing member 460 and the compression system are implanted together.

Figure 24:
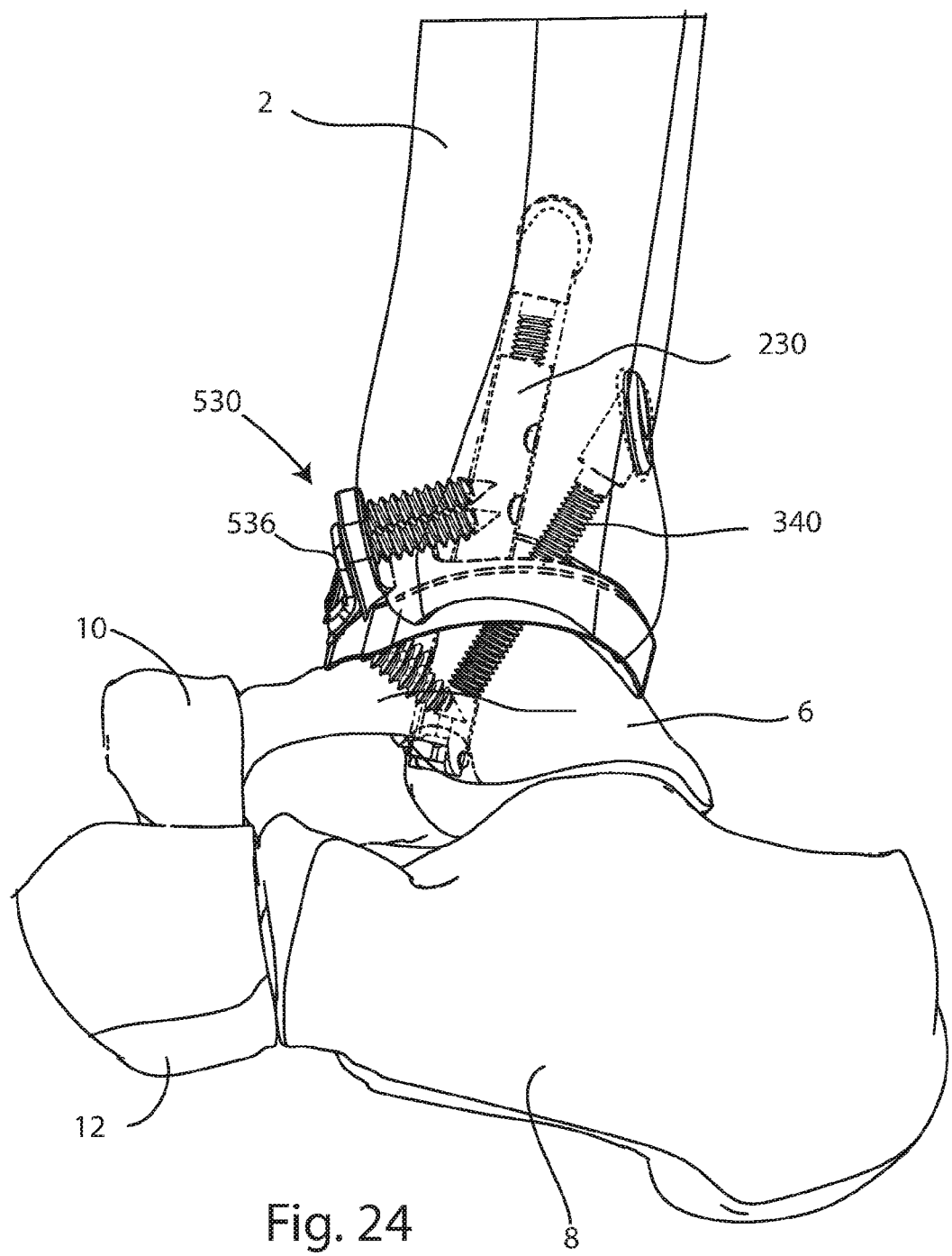

A lateral view in FIG. 24 shows spacing member 530 with supplementary plate 536 implanted in a tibiotalar joint, with a compression bolt system 230, and a supplementary screw 340, implanted to extend through the window 533. The compression bolt system, supplementary screw, plus four fixation members in the form of bone screws provide secure fixation of the system in the tibia and talus. Additionally, the compression bolt system 230 provides compression for increased stability between the tibia and talus.

In one example of an implantation procedure for spacing member 530, it is inserted first into the prepared space between the tibia and talus, from an anterior approach. Next, using guide system 300 as set forth above, the guide wire is inserted along a single trajectory from the tibia exterior surface through the talus to the sinus tarsi. The reamer is used to create a bone bore through the tibia and talus along the trajectory, and standoff 232 with rotatable tab 236 is inserted into the bore. Contact of the tab 236 with the calcaneus or other tissue adjacent the sinus tarsi may trigger deployment of the tab 236 from the insertion configuration to the deployed configuration. Cortical washer 168 is placed at the proximal opening of the bone bore in the tibia, and the compression bolt is inserted and engaged with the standoff to provide compression between the bolt head/cortical washer combination, which bear on the exterior surface of the tibia, and the tab 236, which bears on the exterior surface of the talus. Once the compressive force is applied and the joint is immobilized, the fixation members 540 may be driven through the fixation apertures into the tibia and talus, and the supplementary plate 536 attached to the spacing member 530 to prevent screw backout. The supplementary screw 340 may be driven into position either before or after securing the spacing member 530 with the fixation members 540. In an alternative embodiment, the supplementary screw may be replaced with a second compression bolt system.

The spacing members disclosed herein may implanted via anterior or lateral access. If previous procedures have resulted in several anterior incisions, the lateral approach may be preferred to avoid wound complication. If a lateral approach is chosen, a fibular osteotomy may be performed to allow access to the joint. Joint surfaces may be resected or shaped to prepare for the spacing member. The spacing member is implanted in the prepared area, and then the compression system is implanted as set forth previously. Obviously, during positioning of the guide system 300 to determine the trajectory for the standoff and bolt, the trajectory must be oriented to pass through the window or fixation aperture of the selected spacer. Any of the spacing members disclosed herein may be stabilized with one or two compression bolt systems passing through the central window, or through other apertures in the spacer. Additional fixation members passing through apertures in the spacer body and/or flanges may provide added securement and stability. Also, any spacing member disclosed herein may be implanted with bone graft material filling the spacer window.

It is appreciated that the various features of the spacing members disclosed herein may be mixed and matched to provide to form a variety of other alternatives. The spacing members may be flat, anatomically curved, wedge-shaped for deformity or leg length correction, and/or include teeth or other bone engagement features as set forth previously. Attachment features such as flanges, bolt and/or screw apertures, and instrument connection features may be included on any of the spacing member. The spacing members disclosed herein may include any suitable biocompatible material including, but not limited to: plastics including PEEK, carbon fiber reinforced PEEK, glass filled PEEK, UHMWPE, polyurethane, PEKK, and PET; metals and metal alloys including titanium, titanium alloys, stainless steel, cobalt chrome, tantalum, and barium; ceramics including those including alumina, zirconia, zirconium, and silicon nitride; pyrolitic carbon; and coatings including hydroxyapatite, porous titanium, silicon nitride, titanium carbide, and titanium nitride.

Figure 25:
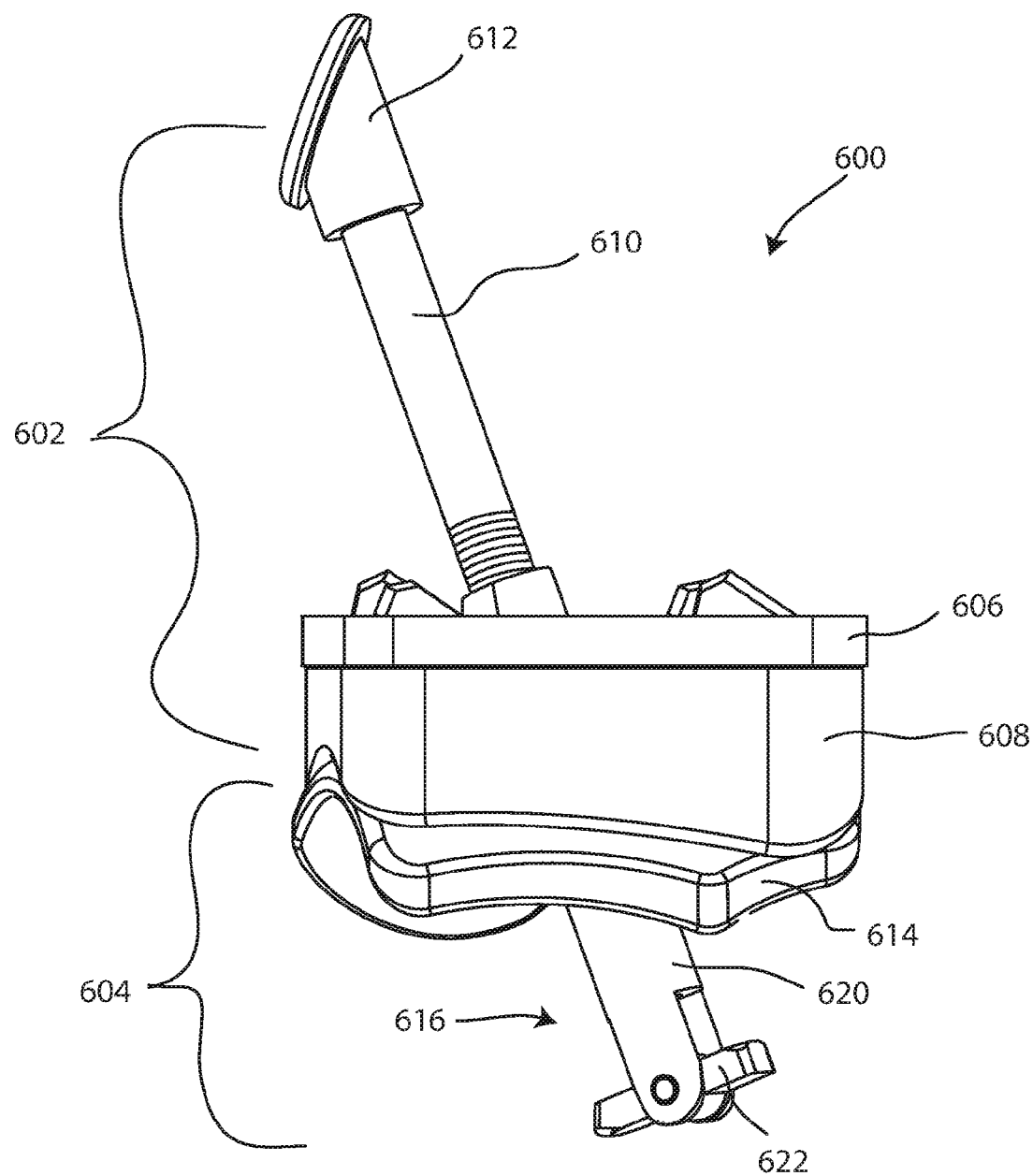
FIG. 25 is an isometric view of an ankle arthroplasty system including a tibial plate, a bearing insert, a talar plate, and tibial and talar anchors.
Figure 26:
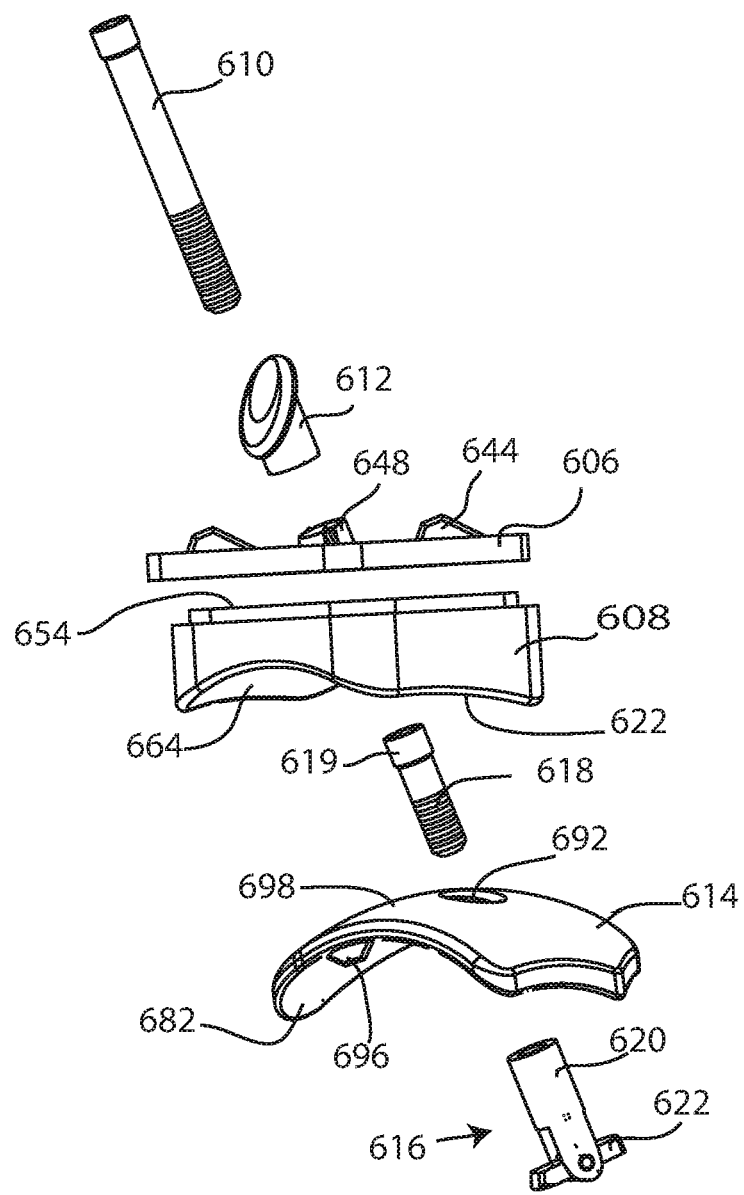
FIG. 26 is an exploded view of the ankle arthroplasty system of FIG. 25.

Ankle arthroplasty systems which may utilize compression bolt fixation as disclosed herein are shown in FIGS. 25-28. FIG. 25 shows a front assembled view of an ankle arthroplasty system 600, while FIG. 26 shows an exploded isometric view. Ankle arthroplasty system 600 includes tibial subsystem 602 and talar subsystem 604. Tibial subsystem 602 includes a tibial plate 606, tibial bearing insert 608, tibial compression bolt 610, and cortical washer 612. When properly implanted in the prepared distal end of a tibia, the tibial compression bolt 610 may be actuated to provide a selected level of compression between the tibial plate and the head of the compression bolt, which may be retained in the cortical washer. Talar subsystem 604 includes talar plate 614, talar anchor 616, and talar compression bolt 618, which is not visible in FIG. 25. Talar anchor 616 further includes standoff 620 and anchoring tab 622. Standoff 620, which may also be referred to as a sleeve, coaxially receives a portion of talar compression bolt 618. When talar subsystem 604 is properly implanted on a talus, talar compression bolt 618 may be actuated to provide a selected level of compression between the talar plate and the talar anchor. As seen in FIG. 25, the subsystems 602, 604 are advantageously implantable along a single trajectory extending through the tibia and talus, which may result in a faster and simpler implantation procedure than required for other ankle arthroplasties.

Tibial plate 606, tibial bearing insert 608 and talar plate 614 may be described as a mobility structure, for when they are implanted between a tibia and a talus they are configured to provide relative motion between the tibia and the talus across the tibiotalar joint. In the embodiment seen in FIGS. 25-28, tibial plate 606 has a polygonal shape which is approximately rectangular, having a superior side 630, an inferior side 632, an anterior end 634, a posterior end 636, a medial end 638 and a lateral end 640. Tibial plate superior side 630 includes a substantially planar bone-engaging surface 642, on which are formed a plurality of teeth 644 configured to penetrate the adjacent bone and prevent rotation of the plate. An angled lumen 646 extends between the superior and inferior sides, encircled by a collar 648 which projects at an angle from the superior side. The lumen 646 and collar 648 are sized and angled to receive the compression bolt at a selected angle. The collar 648 is threaded to threadably engage a distal portion of the compression bolt 610 and to engage with instrumentation as needed. Collar 648 may be referred to as a sleeve, as it coaxially receives a portion of the compression bolt 610. The inferior side 632 includes a raised rim 650 which forms a boundary around a recess 652, into which a protruding portion of the bearing insert is shaped to fit.

Bearing insert 608, which may be described as an articular insert, is sized and shaped to fit into the recess of the tibial plate with sufficient clearance for a snap-fit connection. The outer perimeter of the bearing insert matches the outer perimeter of the tibial plate, such that when they are fitted together relatively smoothly continuous anterior, posterior, medial and lateral sides are formed. The insert includes a superior side 654, which further includes a protruding portion 656 surrounded by a stepped-down rim 658. Thus, when the superior side 654 of the insert 608 is urged against the inferior side 632 of the tibial plate 606, the protruding portion 656 complementarily fits into the recess 652, and the raised rim 650 complementarily fits against the stepped down rim 658. A blind hole 660 extends into the bearing insert 608 from the superior side 654, positioned to line up with the lumen 646 and receive a portion of the tibial compression bolt when implanted. An inferior side 662 includes a tibial bearing surface 664 which may be shaped to complementarily articulate with a talar bearing surface formed on the talar plate. The tibial bearing surface 664 is concavely curved between an anterior 666 and posterior 668 end, and is also concavely curved between a medial 670 and a lateral 672 end. The shapes and radii of the bearing surface curves may vary to meet patient anatomical constraints, meet patient motion needs, and/or to best replicate natural ankle articulation. A thickness, or height h of the bearing insert is measured perpendicular relative to the superior side 654, and varies across the insert in accordance with the curvature of the bearing surface, and may also vary to provide deformity correction or leg length adjustment as needed. The bearing insert 608 may include a biocompatible plastic material, such as PEEK, carbon fiber reinforced PEEK, glass filled PEEK, UHMWPE, polyurethane, PEKK, and PET, among others.

Talar plate 614 has a superior side 680 and an inferior side 682, and a generally irregular perimeter which has an anterior end 684, a posterior end 686, a medial end 688, and a lateral end 690. The perimeter may be shaped to conform to the superior side of the talus or in some embodiments may be more artificially shaped. The inferior side 682 may be shaped to complementarily fit over the talus superior surface. A talar angled lumen 692 extends through the plate between the superior and inferior sides, and is encircled by a collar 694 which protrudes from the inferior side 682. The collar 694 further includes an annular shoulder 695, which retains a head 619 of the talar compression bolt 618 when assembled. A plurality of teeth 696 also protrude from the inferior side to provide stabilization and anti-rotational support to the plate 614. In other embodiments of the invention, keels, ridges, posts, pegs or other bone-engagement features may be included in place of or in addition to teeth 644 and 696. The superior side 680 includes a talar bearing surface 698, which is shaped to bear against the tibial bearing surface 664. The talar bearing surface 698 is convexly curved between the anterior 684 and posterior 686 end, and is also convexly curved between a medial 688 and a lateral 690 end. The shapes and radii of the bearing surface curves may vary to meet patient anatomical constraints, meet patient motion needs, and/or to best replicate natural ankle articulation.

It is appreciated that in this and other embodiments of the invention, the relative footprint, lengths, widths, heights and shapes of the plates 606, 614 and insert 608 may vary as needed to fit patient anatomy and/or desired correction; for example, a medial end may be longer than a lateral end or the height of the insert or plates may vary as needed. Similarly, the specific curvatures of the bone-engaging and bearing surfaces may vary to suit patient anatomy and mobility needs. For example, the tibial plate may be curved while the talar plate is generally planar, and vice versa. Also, in other embodiments, the tibial plate may include the tibial bearing surface, while the insert includes the talar bearing surface. In yet other embodiments, the tibial and talar plates may include the tibial and talar bearing surfaces, respectively, and no separate insert may be included. The tibial and talar plates disclosed herein may include any biocompatible metal or metal alloy, including but not limited to: titanium, titanium alloys, stainless steel, cobalt chrome, tantalum, and barium. The plates could also include biocompatible plastic material, such as PEEK, which may be filled. The bone-facing surfaces of the tibial and talar plates may further include coatings or treatments including but not limited to: hydroxyapatite, porous titanium, silicon nitride, titanium carbide, and titanium nitride.

Figure 27:
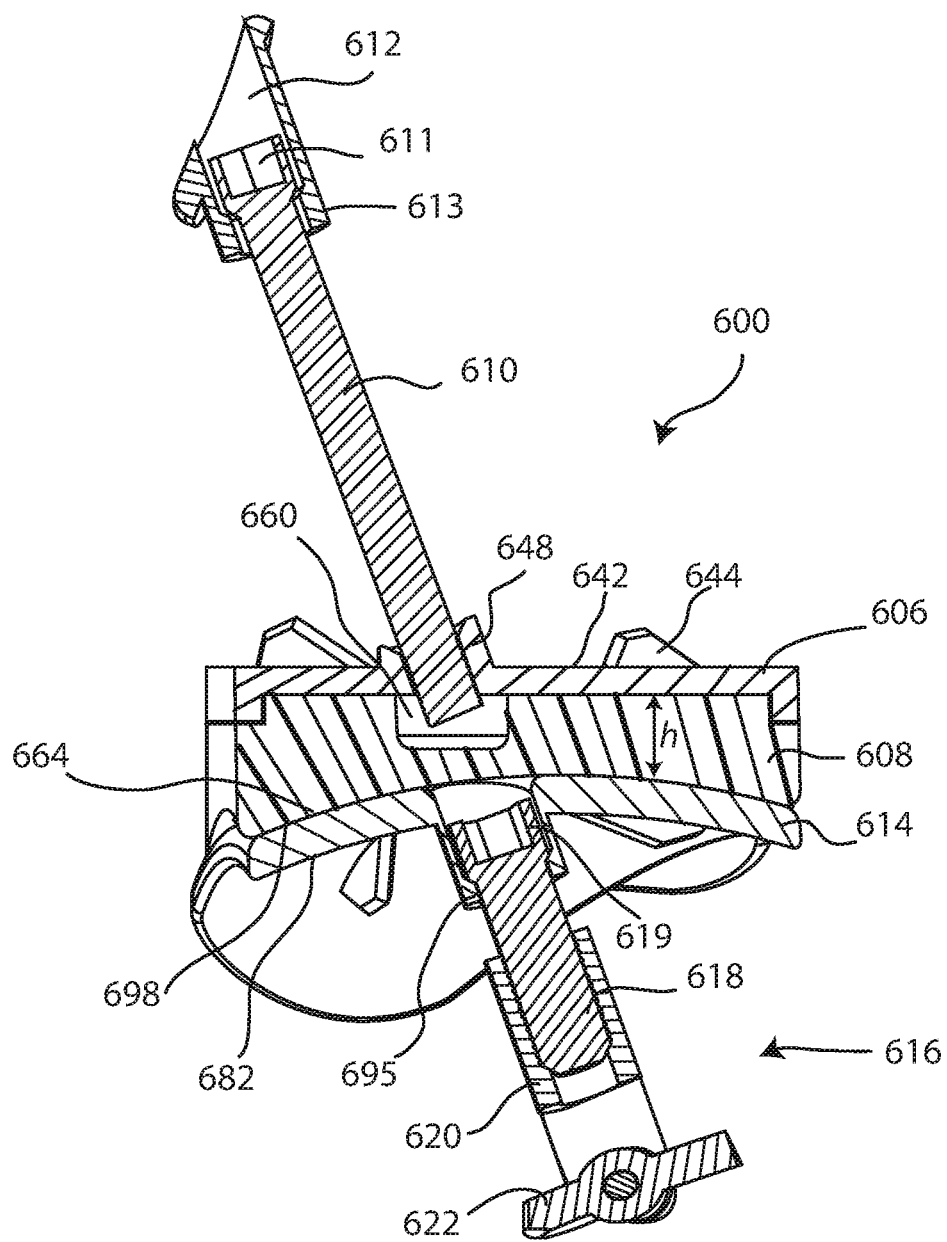
FIG. 27 is a cross-sectional view of the ankle arthroplasty system of FIG. 25.
Figure 28A:
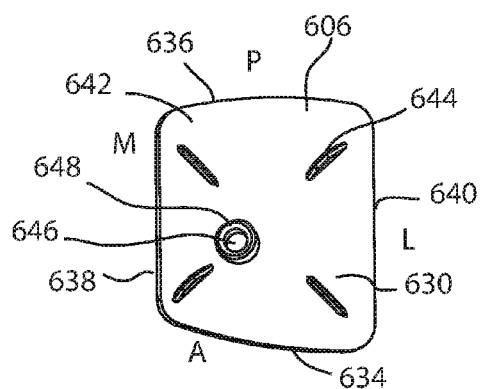
FIG. 28A is a superior view of the tibial plate of the ankle arthroplasty system of FIG. 25.
Figure 28B:
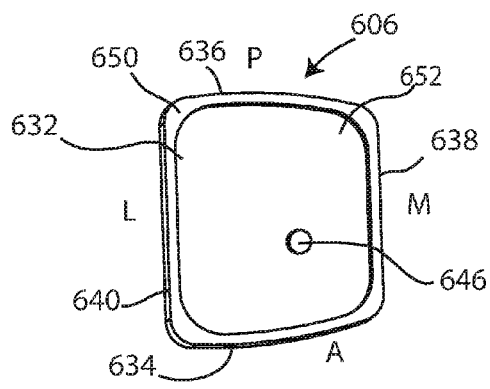
FIG. 28B is an inferior view of the tibial plate.
Figure 28C:
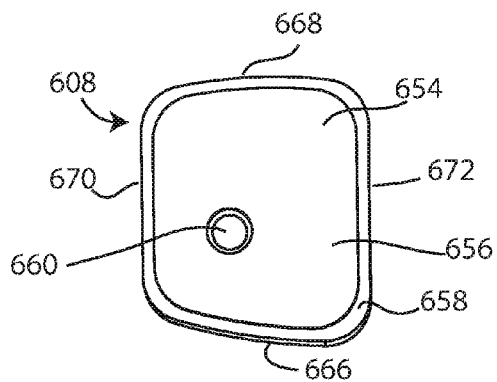
FIG. 28C is a superior view of the bearing insert of the ankle arthroplasty system of FIG. 25.
Figure 28D:
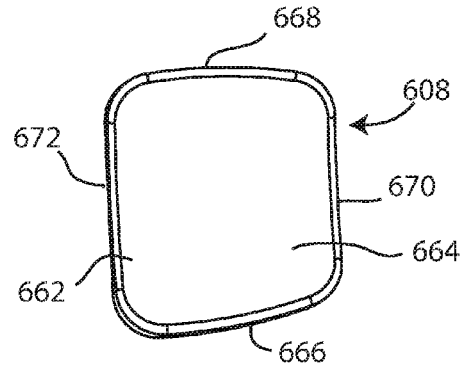
FIG. 28D is an inferior view of the bearing insert.
Figure 28E:
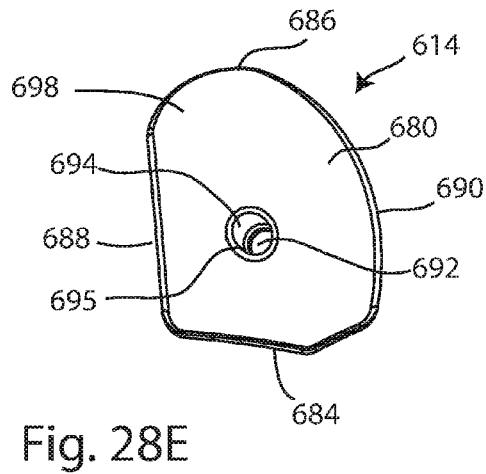
FIG. 28E is a superior view of the talar plate of the ankle arthroplasty system of FIG. 25.
Figure 28F:
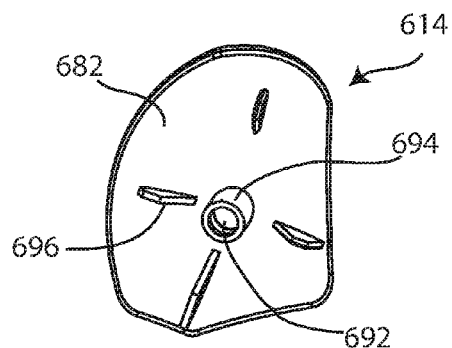
FIG. 28F is an inferior view of the talar plate.
Figure 29A:
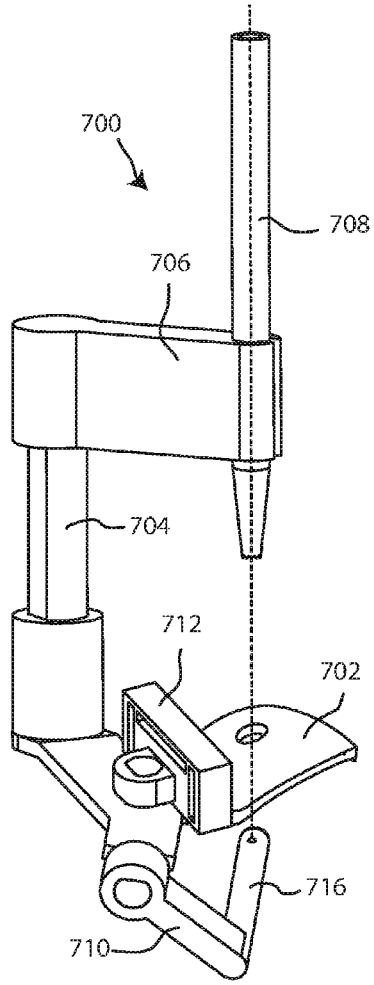
FIG. 29A is an isometric view of a modular targeting guide system for implantation of the arthroplasty system of FIG. 25, including a talar guide, an upright, a guide arm, a guide sleeve, a sinus tarsi guide, and a cutting guide.
Figure 29B:
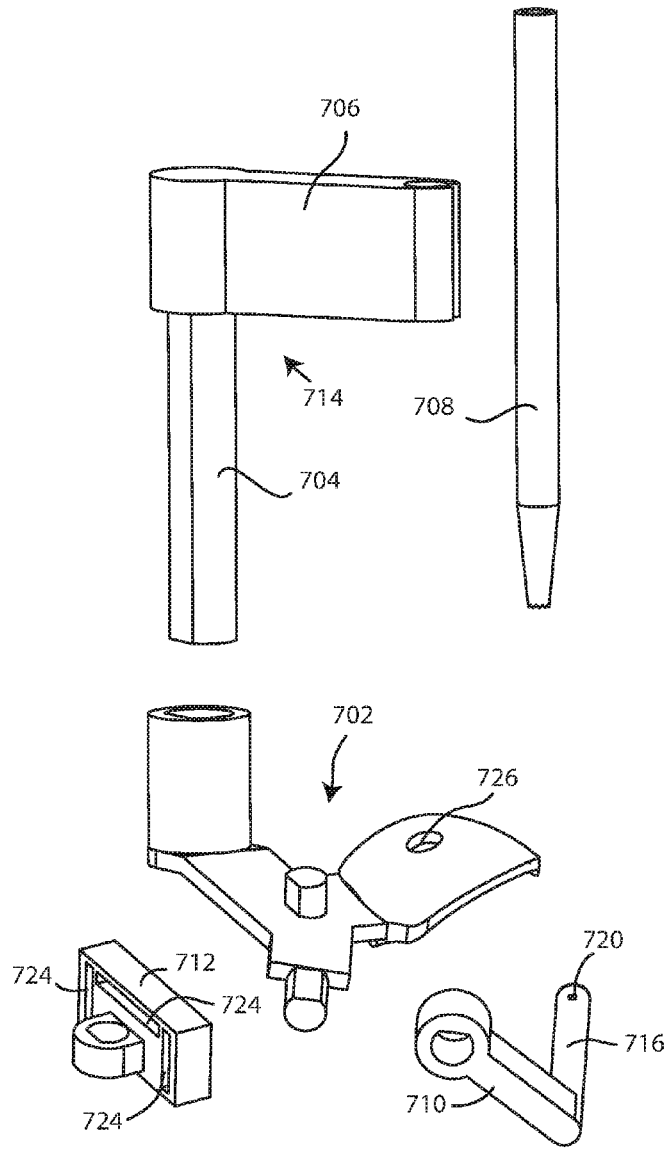
FIG. 29B is an exploded view of the targeting guide system of FIG. 29A.

Referring specifically to FIG. 27, a cross-sectional anterior view of an assembled configuration of arthroplasty 600 is shown. Tibial compression bolt 610 extends between cortical washer 612 and tibial plate 606, and is threadably engaged in collar 648 of the tibial plate. When tibial compression bolt 610 is rotated, the distance between the cortical washer 612 and tibial plate 606 may be adjusted to provide a selected level of compression between the cortical washer 612 and the tibial plate 606. Bearing insert 608 is snap-fit into tibial plate 606. Talar compression bolt 618 extends between talar plate 614 and talar anchor 616, and is threadably engaged in the standoff 620 of the talar anchor 618. When talar compression bolt 618 is rotated, the distance between the talar anchor 618 and talar plate 614 may be adjusted to provide a selected level of compression between the anchoring tab 622 and the talar plate 614. Tibial bearing surface 664 and talar bearing surface 698 are positioned to articulate relative to one another.

FIGS. 29-33 illustrate methods and instruments for preparation and implantation of ankle arthroplasty system 600. Referring to FIGS. 29A and 29B, an ankle arthroplasty guide system 700 is shown in assembled and exploded views, the modular system including talar guide 702, upright 704, guide arm 706, sleeve 708, sinus tarsi guide 710, and cutting guide 712. The cutting guide can come in a variety of heights, the chosen height depending on the height h of the bearing insert to be implanted. The upright 704 and guide arm 706 together form a drill guide 714. To prepare a tibiotalar joint for an arthroplasty implantation, an anterior incision is made and minimal cartilage is removed from the superior side of the talus to create room for the talar guide.

The talar guide 702 is inserted and positionally adjusted until it rests in the same position preferred for the talar plate of the implant. The talar guide may be attached to a framework or table, or otherwise stabilized to hold the preferred position. A targeting arm 716 of the sinus tarsi guide is inserted into the sinus tarsi and the sinus tarsi guide 710 is coupled to the talar guide. The drill guide 714 is coupled to the talar guide 702. In one embodiment, the couplings are all fixed and non-rotatable so that the sinus tarsi guide, drill guide 714 and cutting guide 712 may all be coupled to the talar guide 702 in specific fixed relationships. In other embodiments, one or more of the couplings may be adjustable.

Figure 30:
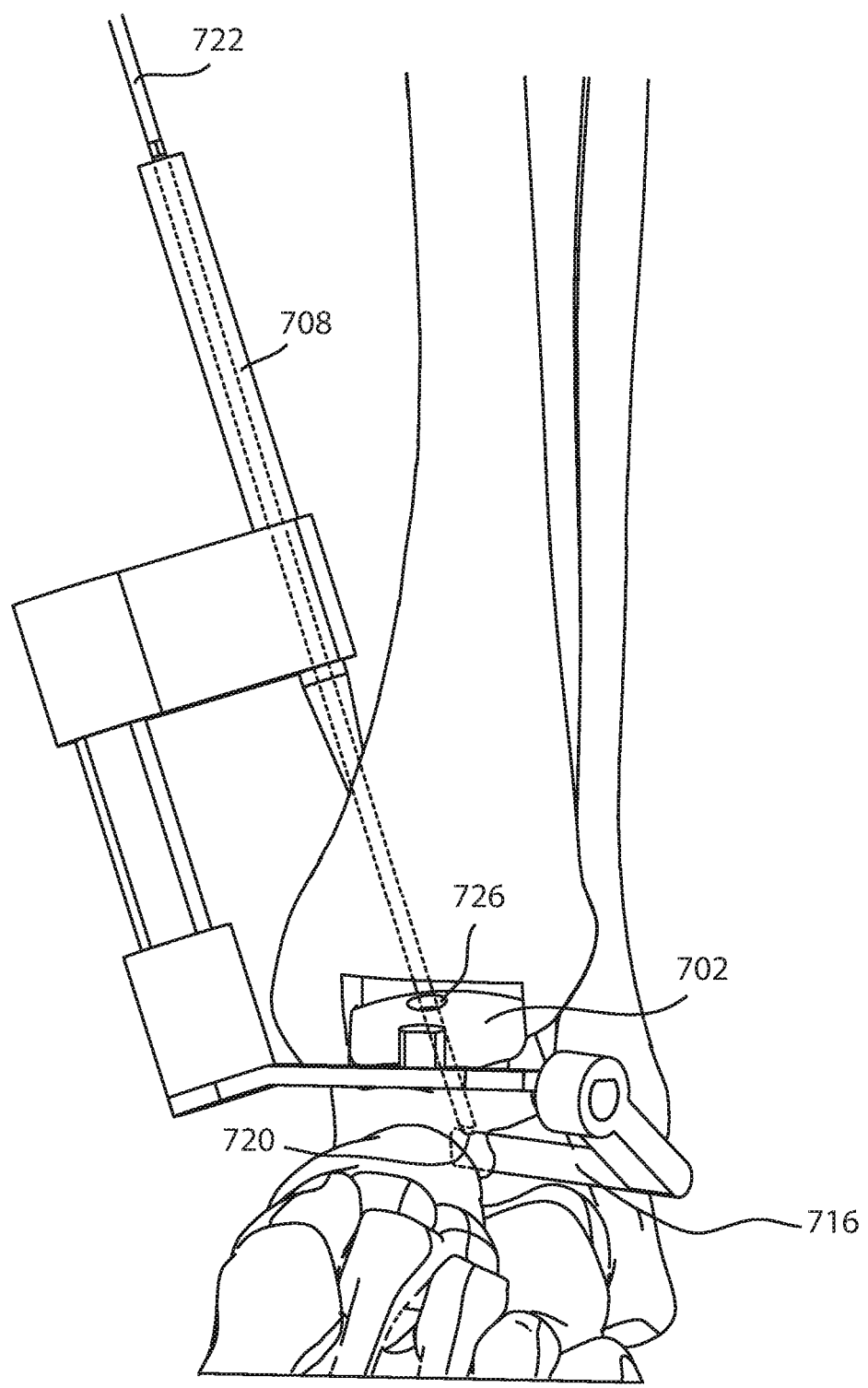
Figure 31:
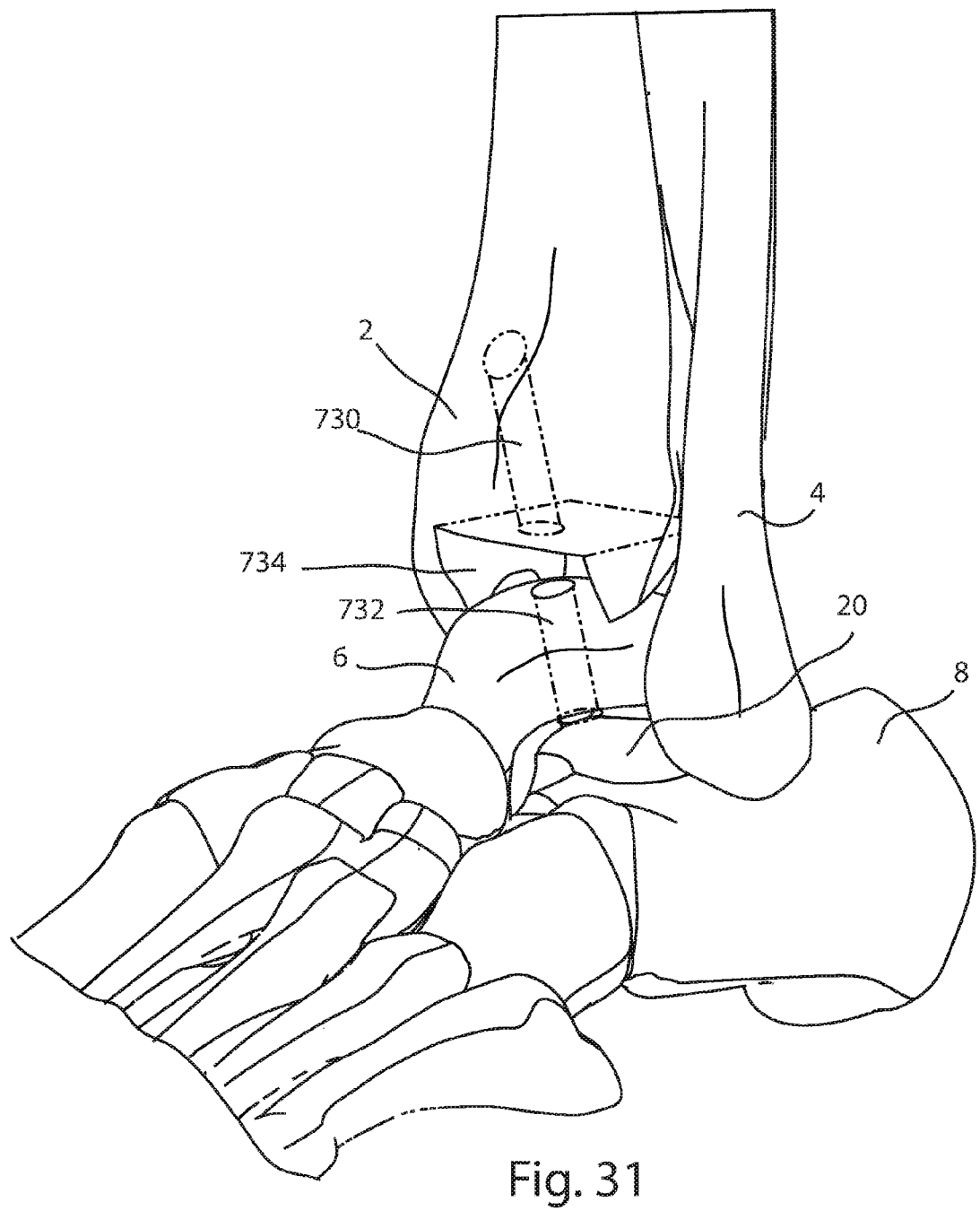

The sleeve 708 is inserted into the drill guide 714. At this point, as illustrated by the dashed line in FIG. 29A, a single straight trajectory may pass longitudinally through the sleeve, through an opening 726 in the talar guide 702, to a targeting point 720 on the sinus tarsi arm 716. This allows for placement of the tibial and talar plate anchoring systems along a single trajectory, and provides the potential for future conversion from arthroplasty to fusion by removal of the arthroplasty system 600 and replacement with a compression bolt system such as system 100, 160, 180, 230, or 250, for example. A guide wire 722 is inserted through sleeve 708 and inserted partially through the tibia. Insertion is temporarily stopped when a marking on the guide wire 722 lines up with the top of the sleeve 708. Next, the cutting guide 712 is placed on the talar guide 702. An oscillating saw or other cutting means is used to remove tibial bone adjacent to the tibial guide, guided by slots 724 on the cutting guide 712. After the indicated tibial bone is removed, the cutting guide 712 is removed, and insertion of the guide wire 722 can continue. As seen in FIG. 30, the guide wire 722 is inserted along the trajectory through the remainder of the tibia, through the opening 726 in the talar guide, and through the talus to the targeting point 720 on the sinus tarsi arm 716. The sleeve 708 and drill guide 714 may be removed, and a reamer (not shown) is inserted over the guide wire to ream a continuous bore through the tibia and talus, stopping when the reamer enters the sinus tarsi. The talar guide 702, reamer and guide wire 722 are removed, leaving the joint area prepared for implantation of the arthroplasty system. FIG. 31 illustrates the prepared area, which includes a first or tibial bone bore 730, a second or talar bone bore 732, and tibial resection 734. As set forth previously, the first 730 and second 732 bone bores follow a single straight trajectory through the tibia and talus. In the example shown, the tibial bone bore is non-parallel with the intramedullary canal of the tibia.

Figure 32A:
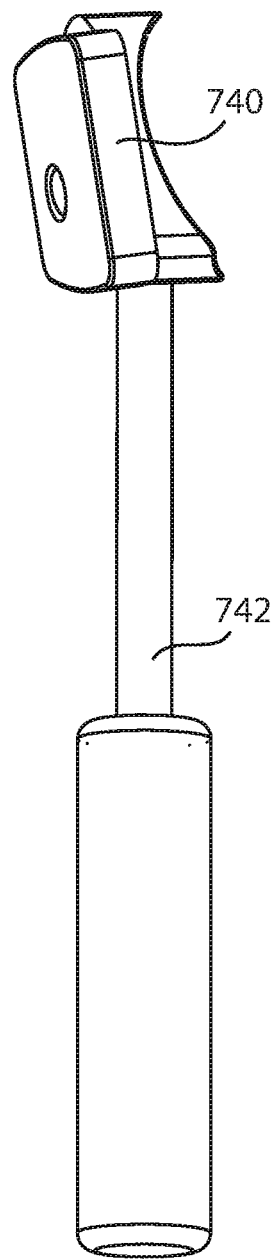
FIG. 32A is an isometric view of an ankle arthroplasty trial.
Figure 32B:
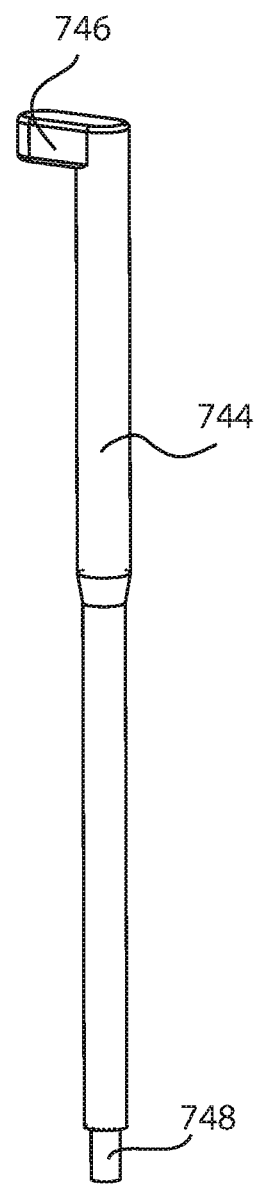
FIG. 32B is an isometric view of a tamp.

After preparation of the joint area, a trial or trials may be inserted into the tibial resection to determine the proper size and configuration for the tibial plate, the talar plate, and the bearing insert. FIG. 32A illustrates an exemplary trial 740 mounted on an inserter 742. Trials of various sizes and shapes may be inserted until the optimal configuration of tibial plate, bearing insert, and talar plate is determined. A tamp 744 including a handle 746 and a threaded tip 748 is illustrated in FIG. 32B.

Figure 33:
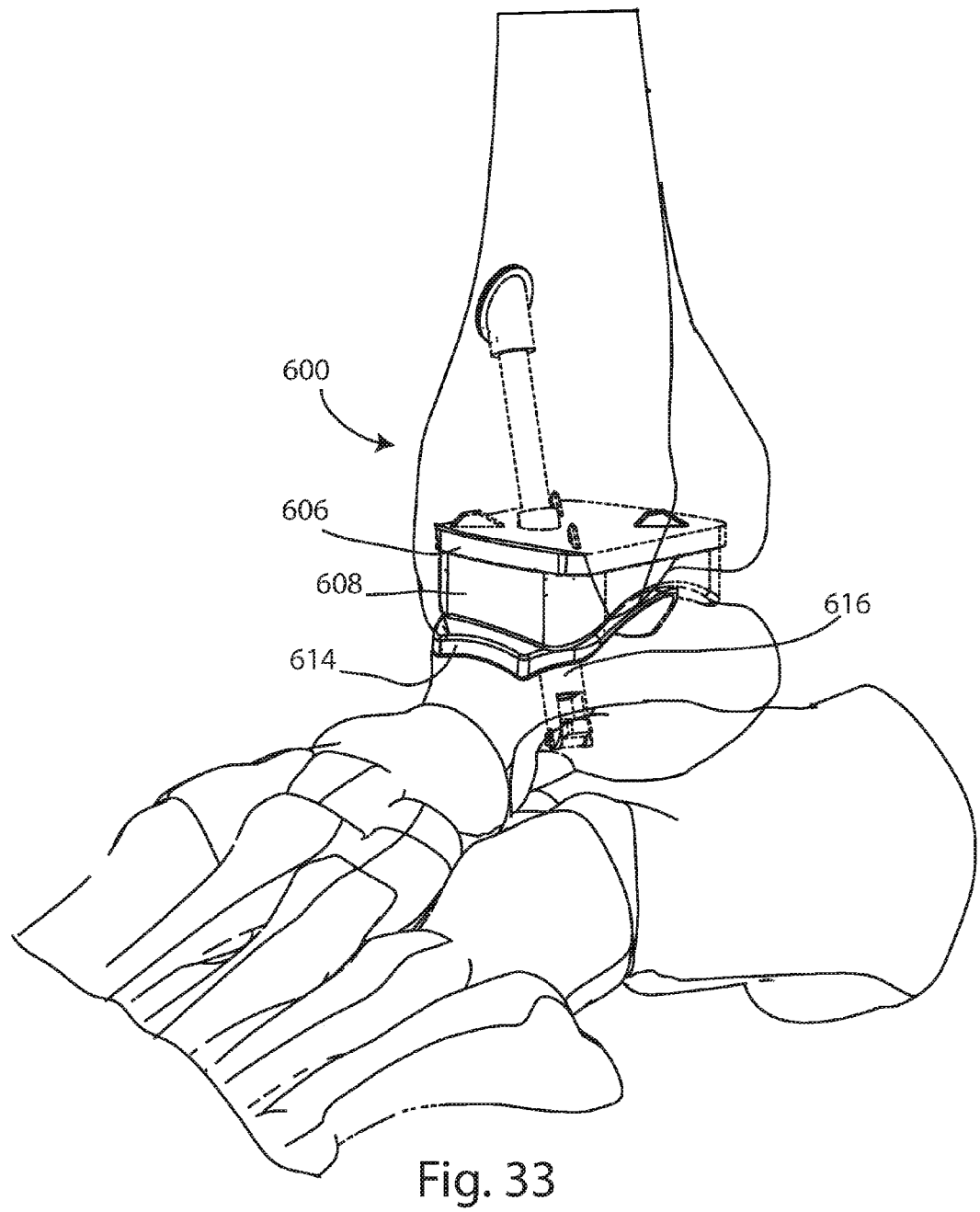

FIG. 33 illustrates a lateral isometric view of ankle arthroplasty system 600 implanted into a prepared space in an ankle. With reference to FIGS. 26, 27 and 31-33, a method for implantation of system 600 is described. Talar anchor 616, with anchoring tab 622 in an insertion configuration, is threaded onto the tamp tip 748, and inserted through the tibial and talar bone bores, into the sinus tarsi. When anchoring tab 622 encounters the calcaneus, it rotates into the deployed configuration. The surgeon may pull back slightly on the tamp handle 746 to seat the anchor tab 622 against the inferior surface of the talus and feel that the tab is deployed. The tamp 744 is unthreaded and removed.

The talar plate 614 is inserted next, and positioned over the talus so that the protruding collar 694 fits into the opening into the talar bone bore and the angled lumen 692 is continuous with the bone bore. The talar compression bolt 618 is fitted onto a bolt driver (not shown, but may be the same as bolt driver 324) and inserted through both bone bores, through the angled lumen 692 and coaxially received into the standoff portion 620 of the talar anchor 616. The head 619 of the compression bolt 618 is retained by the annular shoulder 695 of the talar plate 614. The compression bolt 618 is threadably engaged with the standoff 620 and selectively tightened until a preferred level of compression is reached between the talar plate 614 and the anchoring tab 622. During compression, the teeth 696 will engage in the adjacent talar surface.

The tibial plate 606 is inserted into the tibial resection, and the threaded tamp tip 748 is threadably engaged in the tibial plate collar 648. The tamp is pulled proximally to seat the tibial plate teeth 644 into the resected tibial surface. The tamp 744 is unthreaded and removed. The cortical washer 612 and tibial compression bolt 610 are implanted; the cortical washer 612 is fitted into the proximal opening of the tibial bone bore where it may congruently bear against the exterior surface of the tibia. The bolt 610 is inserted through the washer, and a washer shoulder 613 retains the bolt head 611. The bolt 610 is coaxially received in the tibial plate collar 648, the bolt threads are engaged with the tibial plate collar threads, and the bolt driver such as driver 324 is used to tighten the bolt. As the bolt is tightened, the distance between the cortical washer 612 and tibial plate 606 decreases, providing compression. The bearing insert 608 in inserted between the tibial plate 606 and the talar plate 614, and snapped into the tibial plate with the protruding portion 656 of the insert fitting into the recess 632 of the tibial plate.

In another embodiment, a screw may be used instead of the talar anchor/bolt combination to attach the talar plate 614 to the talus. In this embodiment, no hardware is positioned in the sinus tarsi. The screw is inserted through the angled lumen 692 and threaded into the tibial bone bore. The screw head is retained by the annular shoulder 695 of the talar plate 614.

In yet another embodiment, a retrograde bolt may be used instead of the talar anchor/bolt combination to attach the talar plate 614 to the talus. A bolt may be introduced retrograde through the sinus tarsi, into the tibial bone bore and engaged with the threaded tibial plate collar 648. The bolt head is retained in the sinus tarsi by the distal opening of the tibial bone bore. In this embodiment, no opening in the superior or bearing side of the talar plate is required.

Arthroplasty system 600 may be converted to an arthrodesis system if desired. A spacer shaped to occupy the footprint and height of the tibial plate, bearing insert, and talar plate may be inserted to replace those components, and a single compression bolt, passing through the spacer window, may connect to the talar anchor to provide compression across the joint and provide fusion.

Figure 34A:
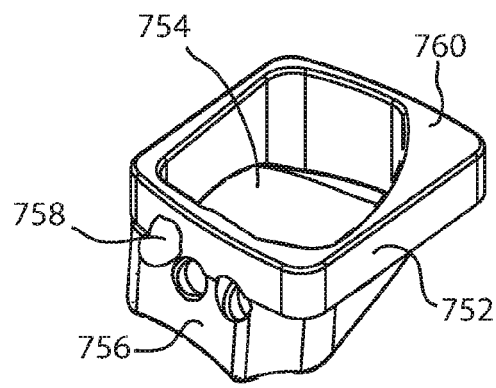
FIG. 34A is an isometric view of a fusion conversion spacing member.
Figure 34B:
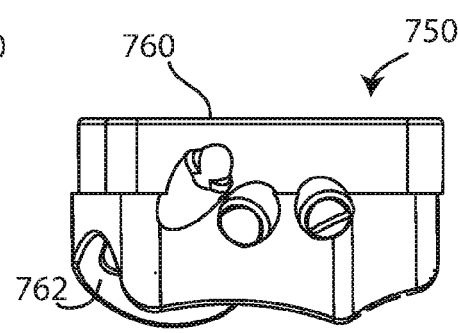
FIG. 34B is an anterior view of the spacing member of FIG. 34A.
Figure 34C:
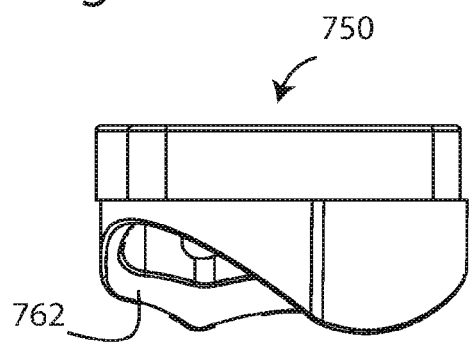
FIG. 34C is a posterior view of the spacing member of FIG. 34A.
Figure 34D:
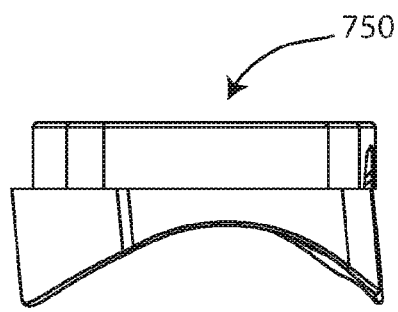
FIG. 34D is a medial view of the spacing member of FIG. 34A.
Figure 34E:
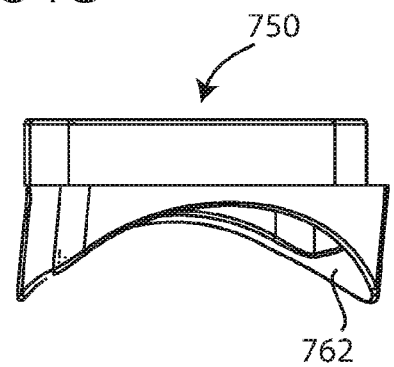
FIG. 34E is a lateral view of the spacing member of FIG. 34A.
Figure 34F:
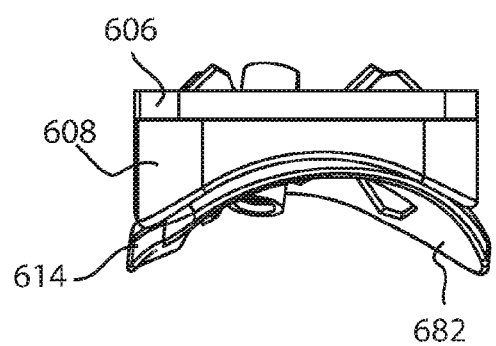
FIG. 34F is a lateral view of the tibial plate, bearing insert, and talar plate of the ankle arthroplasty system of FIG. 25.

FIGS. 34A-34E illustrates several views of a conversion spacer 750, and FIG. 34F illustrates tibial plate 606, bearing insert 608, and talar plate 614 for comparison. Conversion spacer 750 includes spacer body 752 through which extends spacer window 754. An anterior side 756 includes a plurality of fixation apertures 758. A superior, or tibial surface 760 is generally flat, shaped to complementarily fit into the tibial resection 734 seen in FIG. 31. An inferior, or talar surface 762 is anatomically shaped to complementarily fit over the talus, similar to inferior surface 682 of talar plate 614. An overall height, measured from the talar surface 762 to the tibial surface 760, may fill the tibial resection 734 and/or provide deformity correction or leg length discrepancy correction as needed. As with other spacer members disclosed herein, conversion spacer may be angled or wedge-shaped in any direction for deformity correction or leg length discrepancy correction as needed.

With reference to FIGS. 26, 31-33 and 35-36, a method for conversion from ankle arthroplasty to arthrodesis is described. The ankle joint is accessed from an anterior approach, and bearing insert 608 is removed. The tibial compression bolt is accessed on the medial side of the tibia, unscrewed from the tibial plate 606 using a driver such as driver 324, and the cortical washer 612 and tibial compression bolt are removed. An osteotome may be used to loosen the tibial plate, and the tibial plate 606 is removed anteriorly. The talar compression bolt 618 is unscrewed and removed. The talar plate 614 is loosened, and removed. Talar anchor 616 does not have to be removed; it may remain anchored in the sinus tarsi and form the anchor for the arthrodesis system. However, if desired, the anchor tab 622 may be rotated into the insertion configuration, and the threaded tamp 744 used to remove the anchor through the medial tibial opening.

Figure 35:
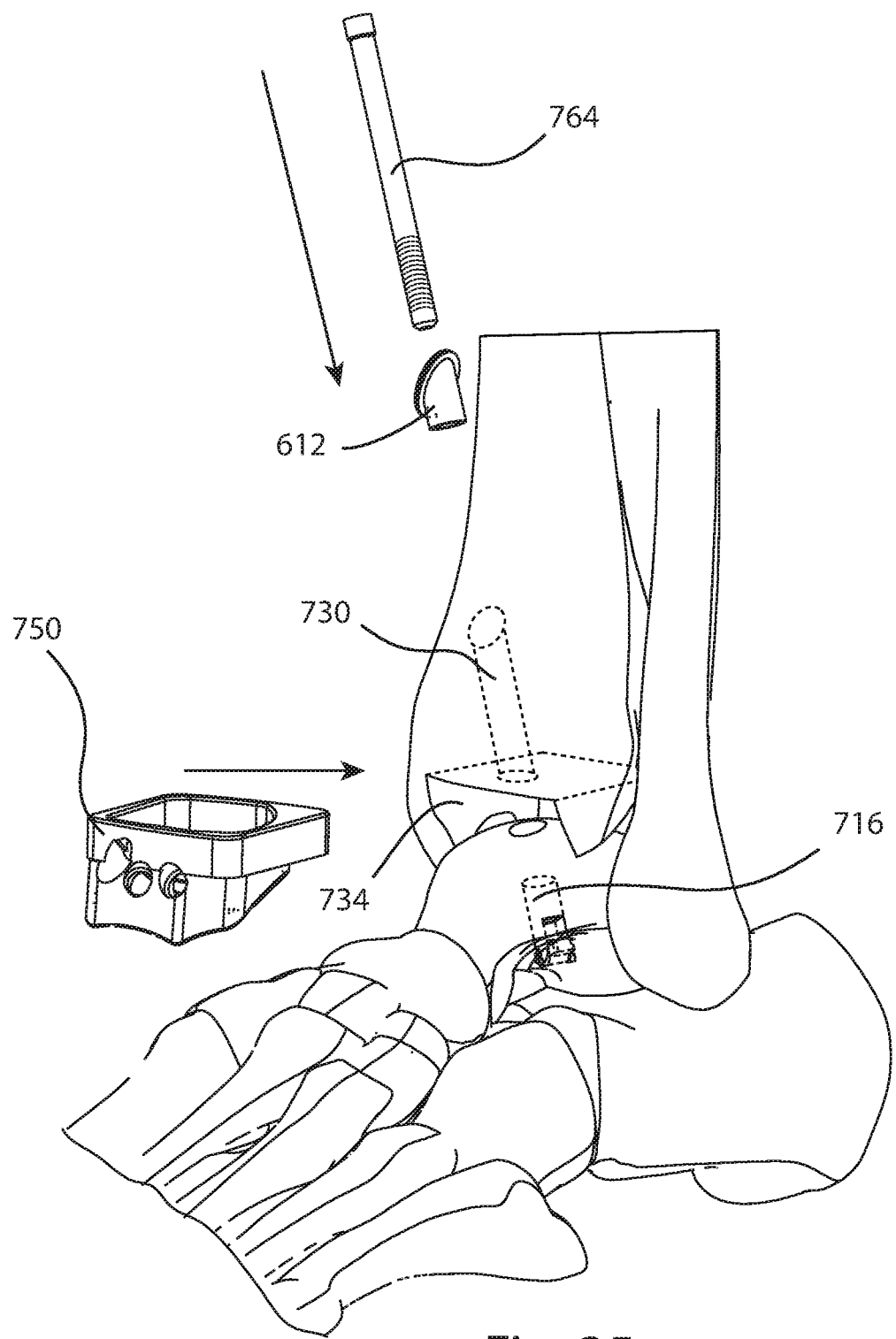
Figure 36:
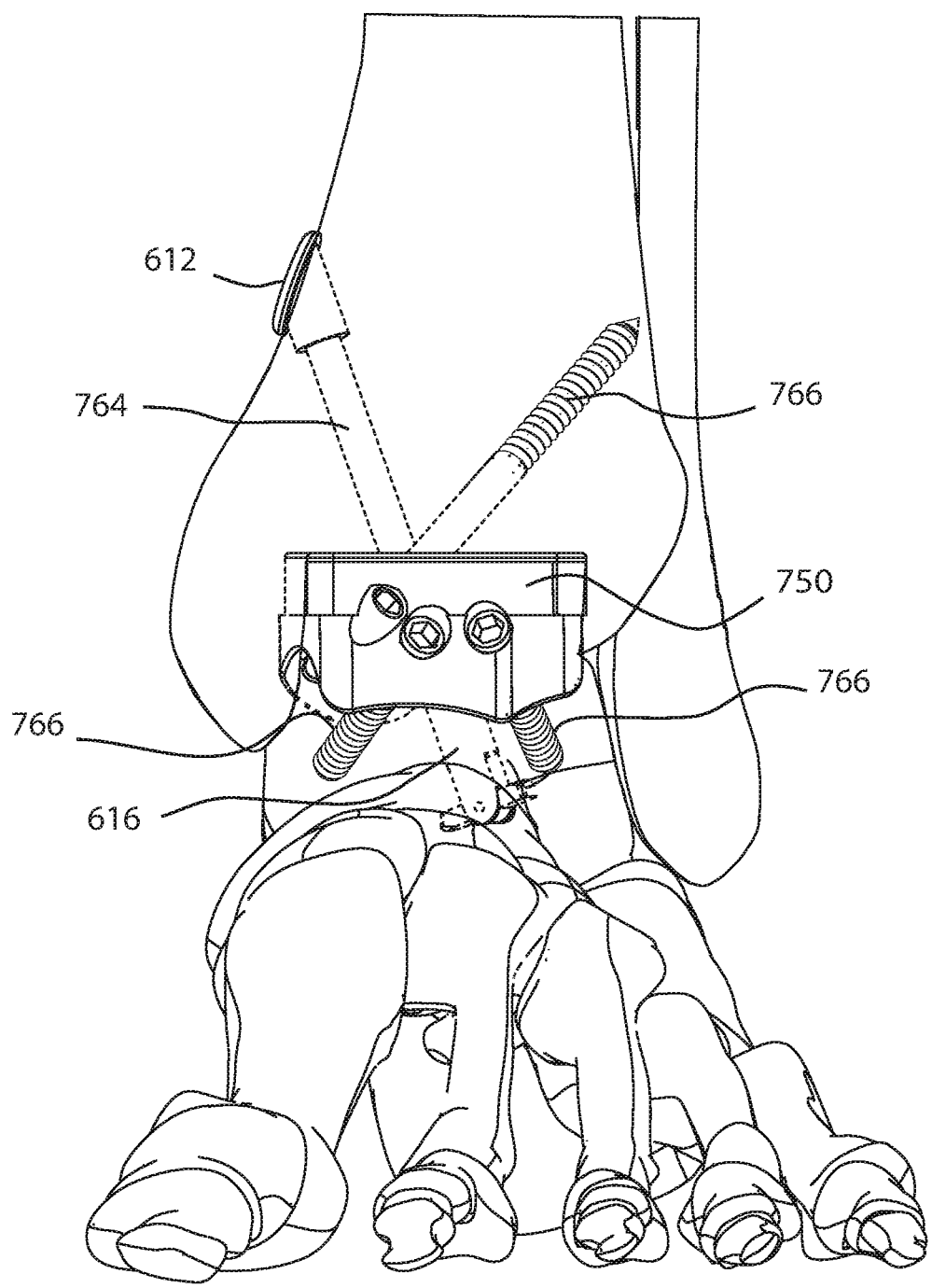

Referring to FIGS. 35 and 36, with all arthroplasty components removed except the talar anchor 616, conversion spacer 750 may be inserted into the resected area 734. Bone graft material may be inserted into window 754 and spacer 750 is inserted into the resected area and fitted over the talus. A compression bolt 764, which is of sufficient length to span from the talar anchor 616 to the medial tibial opening, is inserted with a cortical washer 612 and coaxially engaged with the talar anchor 616. Compression bolt 764 is tightened until the preferred level of compression across the joint is reached, substantially preventing relative motion between the tibia and the talus. Supplementary fasteners 766 are installed through the fixation apertures 758 as desired for additional fixation. In place of, or in addition to, the fasteners 766, other supplementary screws or bolts may be implanted, similar to the fusion embodiments seen in FIGS. 17 and 24.

Figure 37:
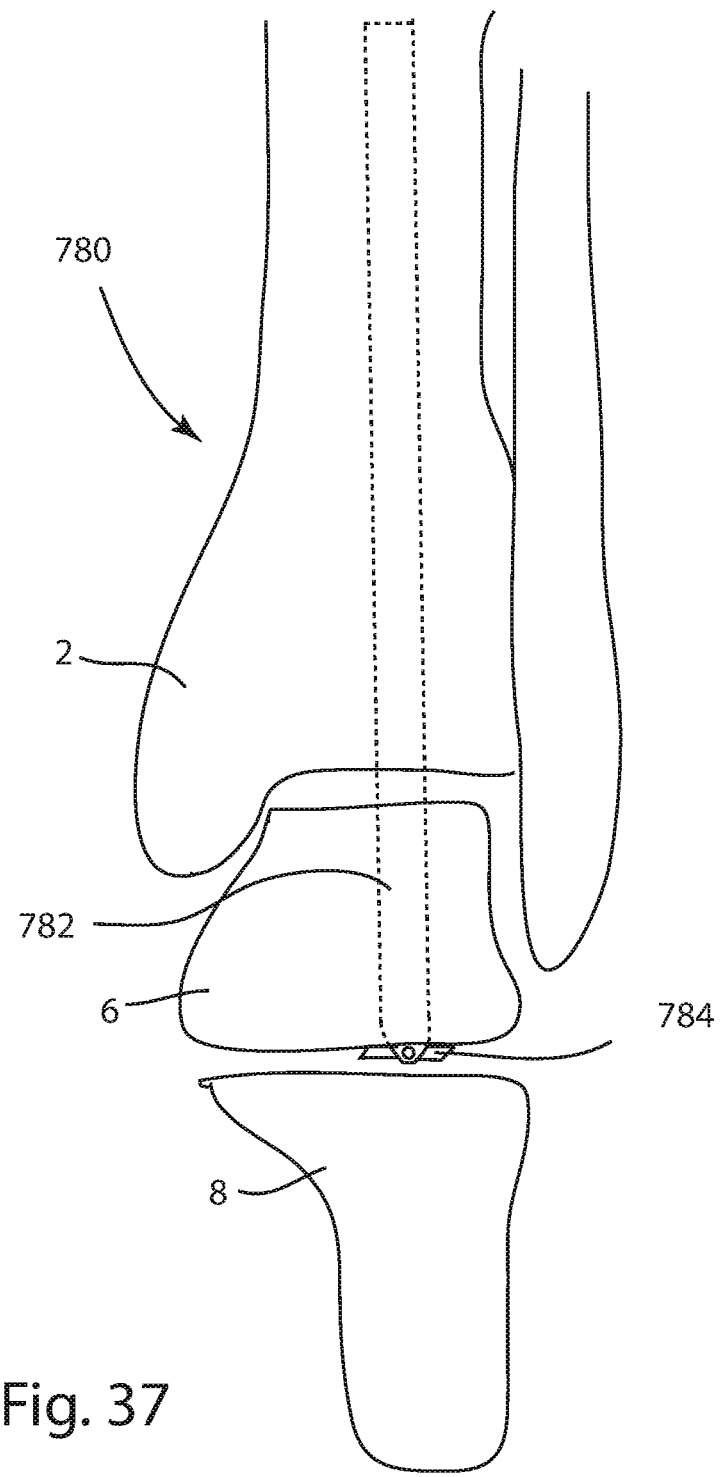

Another embodiment of an ankle arthrodesis device includes an intramedullary nail that is anchored via a toggle or nut on the underside of the talus. Referring to FIG. 37, bone fixation system 780 includes intramedullary nail 782 and anchor 784. The intramedullary nail 782 is introduced antegrade from the proximal end of the tibia, thus avoiding both retrograde insertion, and placement across the subtalar joint. The anchor 784 may be a nut or a toggle and may incorporate any of the toggle anchor features as set forth above with reference to FIGS. 6-11D. The intramedullary nail 782 may further include a standoff and a compression bolt, as set forth above at least with reference to FIGS. 2-11D, to provide compression between the anchor and a proximal end of the intramedullary nail at the proximal end of the tibia. This system 780 may provide tibiotalar fusion without relying on poor bone stock in the talus, such as may occur after a failed arthroplasty. Bone fixation system 780 may be implanted in combination with any of the spacing members disclosed herein to together provide compression and structural load-bearing support. In another embodiment, an arthroplasty system disclosed herein may also be secured with intramedullary nail 782 and anchor 784.

The present invention may be embodied in other specific forms without departing from its spirit or essential characteristics. It is appreciated that various features of the above-described examples can be mixed and matched to form a variety of other alternatives. By way of non-limiting example, any of the compression systems disclosed herein may be implanted in combination with any of the spacers. It is also appreciated that any of the compression systems and/or spacers and/or mobility structures may be configured to provide fusion or motion of other joints, including at least those of the foot and wrist. Any of the compression bolt systems may be configured to compressively join two bones or bone portions together. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method for fusing a tibio-talar joint between an inferior end of a tibia and a superior side of a talus, the talus having a sinus tarsi adjacent to an inferior side of the talus, the method comprising:
inserting an intramedullary nail into the tibia along a superior-inferior longitudinal axis, the intramedullary nail having a proximal end and a distal end and a nail body extending longitudinally therebetween along a nail axis, an external diameter of the nail body perpendicular to the nail axis, and an anchor rotatably attached to the distal end of the intramedullary nail;
positioning the nail body to intersect the inferior end of the tibia;
extending the nail body across the tibio-talar joint;
inserting the intramedullary nail to extend through the talus along the superior-inferior longitudinal axis, the nail body intersecting the superior side and the inferior side of the talus;
positioning the distal end of the intramedullary nail to project into the sinus tarsi; and
rotating the anchor to extend transverse to the superior-inferior longitudinal axis and protrude beyond the nail body external diameter.

2. The method of claim 1, wherein the anchor has a first end and a second end and a length extending therebetween, the method further comprising rotating the anchor so that the anchor length is coaxial with the nail body.

3. The method of claim 2, further comprising positioning the anchor first end within the nail body.

4. The method of claim 2, wherein the length of the anchor is greater than the nail external diameter, wherein rotating the anchor to extend transverse to the superior-inferior longitudinal axis further comprises positioning the first and second ends of the anchor to protrude beyond the nail body external diameter.

5. The method of claim 4, wherein the intramedullary nail further comprises a pair of extensions projecting longitudinally from the distal end and a gap formed between the pair of extensions, wherein rotating the anchor further comprises rotating the first end from a position in the gap to a position outside the gap.

6. The method of claim 5, wherein a pin extends between the pair of extensions to define an axis of rotation perpendicular to the nail axis, wherein rotating the anchor further comprises rotating the anchor about the axis of rotation.

7. The method of claim 1, wherein a calcaneous is inferior to the talus, wherein rotating the anchor further comprises contacting the calcaneous with the anchor, wherein the contact with the calcaneous urges the anchor to rotate to extend transverse to the superior-inferior longitudinal axis, and wherein the anchor is free from contact with the calcaneous when the anchor is transverse to the superior-inferior longitudinal axis.

8. The method of claim 1, wherein rotating the anchor to extend transverse to the superior-inferior longitudinal axis comprises rotating the anchor to extend approximately perpendicular to the superior-inferior longitudinal axis.

9. The method of claim 1, wherein the intramedullary nail includes surface treatments to promote bone engagement.

10. The method of claim 1, further comprising positioning a spacer between the tibia inferior end and the talus superior side, the spacer comprising a bore, and extending the nail body through the spacer bore.

11. The method of claim 1, wherein the nail body comprises a standoff comprising the distal end and a compression bolt comprising an elongated body terminating in the proximal end, the method further comprising telescopically engaging the standoff with the elongated body of the compression bolt to change a distance between the anchor and the proximal end.

12. The method of claim 11, wherein the standoff includes an opening transverse to the nail axis, the method further comprising implanting a supplementary screw to extend through the opening to stabilize the nail body.

* * * * *